US012344601B2

(12) United States Patent
Riether et al.

(10) Patent No.: US 12,344,601 B2
(45) Date of Patent: *Jul. 1, 2025

(54) (CYANO-DIMETHYL-METHYL)-ISOXAZOLES AND -[1,3,4]THIADIAZOLES

(71) Applicant: Centrexion Therapeutics Corporation, Boston, MA (US)

(72) Inventors: Doris Riether, Biberach an der Riss (DE); Florian Paul Christian Binder, Maselheim (DE); Henri Doods, Warthausen (DE); Stephan George Mueller, Warthausen (DE); Janet Rachel Nicholson, Oberhoefen (DE); Achim Sauer, Ravensburg-Torkenweiler (DE)

(73) Assignee: Centrexion Therapeutics Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/216,669

(22) Filed: Jun. 30, 2023

(65) Prior Publication Data

US 2024/0092769 A1  Mar. 21, 2024

Related U.S. Application Data

(63) Continuation of application No. 17/398,155, filed on Aug. 10, 2021, now Pat. No. 11,725,004, which is a continuation of application No. 16/749,412, filed on Jan. 22, 2020, now Pat. No. 11,084,810, which is a continuation of application No. 16/143,523, filed on Sep. 27, 2018, now Pat. No. 10,570,125, which is a continuation of application No. 15/491,035, filed on Apr. 19, 2017, now Pat. No. 10,112,934, which is a continuation of application No. 14/891,051, filed as application No. PCT/EP2014/060033 on May 16, 2014, now Pat. No. 9,650,370.

(30) Foreign Application Priority Data

May 17, 2013  (EP) .................................... 13168165

(51) Int. Cl.
| | | |
|---|---|---|
| *C07D 417/12* | (2006.01) | |
| *A61K 31/422* | (2006.01) | |
| *C07D 261/04* | (2006.01) | |
| *C07D 261/14* | (2006.01) | |
| *C07D 413/02* | (2006.01) | |
| *C07D 413/12* | (2006.01) | |
| *C07D 413/14* | (2006.01) | |

(52) U.S. Cl.
CPC .......... *C07D 417/12* (2013.01); *A61K 31/422* (2013.01); *C07D 261/04* (2013.01); *C07D 261/14* (2013.01); *C07D 413/02* (2013.01); *C07D 413/12* (2013.01); *C07D 413/14* (2013.01)

(58) Field of Classification Search
CPC .................................................... C07D 417/12
See application file for complete search history.

(56) References Cited

U.S. PATENT DOCUMENTS

| | | |
|---|---|---|
| 3,116,284 A | 12/1963 | Testa |
| 3,117,128 A | 1/1964 | Mooradian |
| 3,577,462 A | 5/1971 | Bruce et al. |
| 3,966,809 A | 6/1976 | Baker et al. |
| 4,257,954 A | 3/1981 | Schmidt et al. |
| 4,535,087 A | 8/1985 | Spatz |
| 4,672,065 A | 6/1987 | Spatz |
| 4,734,125 A | 3/1988 | Gehring et al. |
| 4,859,707 A | 8/1989 | Loftsson et al. |
| 5,256,658 A | 10/1993 | Hsi et al. |
| 5,428,037 A | 6/1995 | Pascal et al. |
| 5,475,130 A | 12/1995 | Sato et al. |
| 5,491,170 A | 2/1996 | Lee et al. |
| 5,571,921 A | 11/1996 | Bender et al. |
| 5,583,147 A | 12/1996 | Ko et al. |
| 5,656,634 A | 8/1997 | Chang et al. |
| 5,834,490 A | 11/1998 | Verde-Casanova et al. |
| 5,847,153 A | 12/1998 | Warpehoski et al. |
| 5,958,940 A | 9/1999 | Rane et al. |
| 5,968,929 A | 10/1999 | Blythin et al. |
| 6,057,371 A | 5/2000 | Glennon |
| 6,176,442 B1 | 1/2001 | Eicher et al. |

(Continued)

FOREIGN PATENT DOCUMENTS

| | | | |
|---|---|---|---|
| CH | 312963 | A | 3/1956 |
| DE | 1080563 | B | 4/1960 |
| DE | 3636278 | A1 | 5/1988 |
| EP | 0628555 | A1 | 12/1994 |
| EP | 0929519 | A1 | 7/1999 |
| EP | 0970046 | A1 | 1/2000 |
| EP | 1790641 | A1 | 5/2007 |
| FR | 2866885 | A1 | 9/2005 |
| FR | 2872813 | A1 | 1/2006 |
| GB | 853799 | A | 11/1960 |
| GB | 884258 | A | 12/1961 |
| GB | 1237126 | A | 6/1971 |
| JP | S6127905 | A | 2/1986 |
| JP | S6127955 | A | 2/1986 |

(Continued)

OTHER PUBLICATIONS

Parikh "Preventive analgesia: Effect of small dose of ketamine on morphine requirement after renal surgery" Journal of Anaesthesiology Clinical Pharmacology, Oct.-Dec. 2011, vol. 27, Issue 4, p. 485-488.*

(Continued)

*Primary Examiner* — David K O'Dell
(74) *Attorney, Agent, or Firm* — Dechert LLP

(57) ABSTRACT

This invention relates to novel (Cyano-dimethyl-methyl)-isoxazoles and -[1,3,4]thiadiazoles and their use as CB2 cannabinoid receptor agonists, pharmaceutical compositions containing the same, and their use for the treatment of CB2 receptor mediated disorders or conditions.

20 Claims, No Drawings

(56) References Cited

U.S. PATENT DOCUMENTS

| | | |
|---|---|---|
| 6,221,866 B1 | 4/2001 | Brendel et al. |
| 6,355,653 B1 | 3/2002 | Trottmann et al. |
| 6,359,009 B1 | 3/2002 | Diehl et al. |
| 6,410,792 B1 | 6/2002 | Connell et al. |
| 6,414,011 B1 | 7/2002 | Hogenkamp et al. |
| 6,437,177 B1 | 8/2002 | Warpehoski et al. |
| 6,453,795 B1 | 9/2002 | Eicher et al. |
| 6,528,529 B1 | 3/2003 | Brann et al. |
| 6,573,278 B2 | 6/2003 | Mittendorf et al. |
| 6,610,711 B2 | 8/2003 | Armer et al. |
| 6,737,418 B2 | 5/2004 | Hogenkamp et al. |
| 6,756,404 B2 | 6/2004 | Livinghouse |
| 6,930,115 B2 | 8/2005 | Fujii et al. |
| 7,476,756 B2 | 1/2009 | Almario-Garcia et al. |
| 7,585,881 B2 | 9/2009 | Edwards et al. |
| 7,595,397 B2 | 9/2009 | Zindell et al. |
| 7,776,897 B2 | 8/2010 | Murakami et al. |
| 7,928,123 B2 | 4/2011 | Berry et al. |
| 7,935,715 B2 | 5/2011 | Berry et al. |
| 8,048,899 B2 | 11/2011 | Bartolozzi et al. |
| 8,173,638 B2 | 5/2012 | Berry et al. |
| 8,178,568 B2 | 5/2012 | Regan et al. |
| 8,299,103 B2 | 10/2012 | Bartolozzi et al. |
| 8,299,111 B2 | 10/2012 | Berry et al. |
| 8,329,735 B2 | 12/2012 | Ermann et al. |
| 8,349,871 B2 | 1/2013 | Bartolozzi et al. |
| 8,362,039 B2 | 1/2013 | Bartolozzi et al. |
| 8,372,874 B2 | 2/2013 | Bartolozzi et al. |
| 8,383,615 B2 | 2/2013 | Hickey et al. |
| 8,546,563 B2 | 10/2013 | Berry et al. |
| 8,629,157 B2 | 1/2014 | Berry et al. |
| 8,735,430 B2 | 5/2014 | Bartolozzi et al. |
| 8,778,950 B2 | 7/2014 | Jones et al. |
| 8,829,034 B2 | 9/2014 | Berry et al. |
| 8,846,936 B2 | 9/2014 | Hickey et al. |
| 8,865,744 B1 | 10/2014 | Riether et al. |
| 8,889,670 B2 | 11/2014 | Bartolozzi et al. |
| 8,957,063 B2 | 2/2015 | Cirillo et al. |
| 9,650,370 B2 | 5/2017 | Riether et al. |
| 10,112,934 B2 | 10/2018 | Riether et al. |
| 10,570,125 B2 | 2/2020 | Riether et al. |
| 11,084,810 B2 | 8/2021 | Riether et al. |
| 11,725,004 B2 | 8/2023 | Riether et al. |
| 2002/0099035 A1 | 7/2002 | Sandanayaka et al. |
| 2004/0067999 A1 | 4/2004 | Block et al. |
| 2004/0152747 A1 | 8/2004 | Chen et al. |
| 2004/0242666 A1 | 12/2004 | Chen |
| 2004/0242913 A1 | 12/2004 | Ducray et al. |
| 2005/0059663 A1 | 3/2005 | Martin et al. |
| 2005/0182108 A1 | 8/2005 | Carson et al. |
| 2005/0222219 A1 | 10/2005 | Chen |
| 2006/0009491 A1 | 1/2006 | Yao et al. |
| 2006/0061726 A1 | 3/2006 | Okuyama |
| 2006/0079557 A1 | 4/2006 | Dolle et al. |
| 2006/0173022 A1 | 8/2006 | Schaper |
| 2007/0021403 A1 | 1/2007 | Abouabdellah et al. |
| 2007/0021430 A1 | 1/2007 | Chen et al. |
| 2007/0093501 A1 | 4/2007 | Kubo et al. |
| 2007/0179126 A1 | 8/2007 | Casellas et al. |
| 2007/0191340 A1 | 8/2007 | Zindell et al. |
| 2007/0213311 A1 | 9/2007 | Li et al. |
| 2007/0270426 A1 | 11/2007 | Chen |
| 2008/0039464 A1 | 2/2008 | Berry et al. |
| 2008/0064690 A1 | 3/2008 | Atkinson et al. |
| 2008/0081342 A1 | 4/2008 | Fung |
| 2008/0081822 A1 | 4/2008 | Berry et al. |
| 2008/0227781 A1 | 9/2008 | Bradney et al. |
| 2009/0163545 A1 | 6/2009 | Goldfarb |
| 2009/0275611 A1 | 11/2009 | Riether et al. |
| 2010/0009964 A1 | 1/2010 | Berry et al. |
| 2010/0029644 A1 | 2/2010 | Riether et al. |
| 2010/0076029 A1 | 3/2010 | Bartolozzi et al. |
| 2010/0081644 A1 | 4/2010 | Bartolozzi et al. |
| 2010/0261708 A1 | 10/2010 | Cirillo et al. |
| 2010/0331304 A1 | 12/2010 | Berry et al. |
| 2011/0071127 A1 | 3/2011 | Berry et al. |
| 2011/0071196 A1 | 3/2011 | Bartolozzi et al. |
| 2011/0124696 A1 | 5/2011 | Regan et al. |
| 2011/0130431 A1 | 6/2011 | Berry et al. |
| 2011/0136869 A1 | 6/2011 | Bartolozzi et al. |
| 2011/0190256 A1 | 8/2011 | Cirillo et al. |
| 2011/0312932 A1 | 12/2011 | Bartolozzi et al. |
| 2011/0312944 A1 | 12/2011 | Bartolozzi et al. |
| 2012/0010184 A1 | 1/2012 | Bartolozzi et al. |
| 2012/0015988 A1 | 1/2012 | Hickey et al. |
| 2012/0071529 A1 | 3/2012 | Ermann et al. |
| 2012/0142666 A1 | 6/2012 | Hickey et al. |
| 2012/0142677 A1 | 6/2012 | Berry et al. |
| 2012/0316173 A1 | 12/2012 | Bartolozzi et al. |
| 2019/0161481 A1 | 5/2019 | Riether et al. |

FOREIGN PATENT DOCUMENTS

| | | |
|---|---|---|
| JP | S61126071 A | 6/1986 |
| JP | 2003155285 A | 5/2003 |
| JP | 2006504796 A | 2/2006 |
| JP | 2006143667 A | 6/2006 |
| JP | 2006525990 A | 11/2006 |
| JP | 2007502828 A | 2/2007 |
| JP | 2007530525 A | 11/2007 |
| JP | 2007530661 A | 11/2007 |
| WO | WO9405628 A1 | 3/1994 |
| WO | WO9407607 A1 | 4/1994 |
| WO | WO9626925 A1 | 9/1996 |
| WO | WO9712683 A1 | 4/1997 |
| WO | WO9712687 A1 | 4/1997 |
| WO | WO9720590 A1 | 6/1997 |
| WO | WO9746556 A1 | 12/1997 |
| WO | WO9808295 A1 | 2/1998 |
| WO | WO9811097 A1 | 3/1998 |
| WO | WO9813340 A1 | 4/1998 |
| WO | WO9838163 A1 | 9/1998 |
| WO | WO9965889 A1 | 12/1999 |
| WO | WO0008015 A2 | 2/2000 |
| WO | WO0100573 A1 | 1/2001 |
| WO | WO0129007 A1 | 4/2001 |
| WO | WO0164651 A1 | 9/2001 |
| WO | WO02051806 A1 | 7/2002 |
| WO | WO02062750 A1 | 8/2002 |
| WO | WO02088089 A1 | 11/2002 |
| WO | WO03037274 A2 | 5/2003 |
| WO | WO03055482 A1 | 7/2003 |
| WO | WO03074493 A1 | 12/2003 |
| WO | WO2004000807 A1 | 12/2003 |
| WO | WO2004014370 A2 | 2/2004 |
| WO | WO2004014825 A1 | 2/2004 |
| WO | WO2004014902 A2 | 2/2004 |
| WO | WO2004018433 A1 | 3/2004 |
| WO | WO2004026301 A1 | 4/2004 |
| WO | WO2004029027 A1 | 4/2004 |
| WO | WO2004042351 A2 | 5/2004 |
| WO | WO2004050643 A2 | 6/2004 |
| WO | WO2004060882 A1 | 7/2004 |
| WO | WO2004099200 A1 | 11/2004 |
| WO | WO2004099205 A1 | 11/2004 |
| WO | WO2005027837 A2 | 3/2005 |
| WO | WO2005040355 A2 | 5/2005 |
| WO | WO2005044797 A1 | 5/2005 |
| WO | WO2005068448 A1 | 7/2005 |
| WO | WO2005077345 A1 | 8/2005 |
| WO | WO2005077368 A2 | 8/2005 |
| WO | WO2005077373 A2 | 8/2005 |
| WO | WO2005085227 A1 | 9/2005 |
| WO | WO2006000031 A1 | 1/2006 |
| WO | WO2006012227 A2 | 2/2006 |
| WO | WO2006030805 A1 | 3/2006 |
| WO | WO2006060461 A1 | 6/2006 |
| WO | WO2006074445 A2 | 7/2006 |
| WO | WO2006080040 A1 | 8/2006 |
| WO | WO2006095159 A1 | 9/2006 |
| WO | WO2006100502 A1 | 9/2006 |
| WO | WO2006117461 A2 | 11/2006 |
| WO | WO2007020502 A2 | 2/2007 |
| WO | WO2007054770 A2 | 5/2007 |

(56) References Cited

FOREIGN PATENT DOCUMENTS

| WO | WO2007070760 A2 | 6/2007 |
|---|---|---|
| WO | WO2007080382 A1 | 7/2007 |
| WO | WO2007102059 A1 | 9/2007 |
| WO | WO2007118041 A1 | 10/2007 |
| WO | WO2007140385 A2 | 12/2007 |
| WO | WO2008014199 A2 | 1/2008 |
| WO | WO2008023159 A1 | 2/2008 |
| WO | WO2008039645 A1 | 4/2008 |
| WO | WO2008048914 A1 | 4/2008 |
| WO | WO2008064054 A2 | 5/2008 |
| WO | WO2008098025 A1 | 8/2008 |
| WO | WO2008104994 A2 | 9/2008 |
| WO | WO2009055357 A1 | 4/2009 |
| WO | WO2009061652 A1 | 5/2009 |
| WO | WO2009077533 A1 | 6/2009 |
| WO | WO2009086303 A2 | 7/2009 |
| WO | WO2009105509 A1 | 8/2009 |
| WO | WO2009140089 A2 | 11/2009 |
| WO | WO2010005782 A1 | 1/2010 |
| WO | WO2010036630 A2 | 4/2010 |
| WO | WO2010036631 A2 | 4/2010 |
| WO | WO2010077836 A2 | 7/2010 |
| WO | WO2010096371 A2 | 8/2010 |
| WO | WO2010147791 A1 | 12/2010 |
| WO | WO2010147792 A2 | 12/2010 |
| WO | WO2011009883 A1 | 1/2011 |
| WO | WO2011035159 A1 | 3/2011 |
| WO | WO2011037795 A1 | 3/2011 |
| WO | WO2011088015 A1 | 7/2011 |
| WO | WO2011109324 A1 | 9/2011 |
| WO | WO2012012307 A1 | 1/2012 |

OTHER PUBLICATIONS

Anisimov, A. V. et al., "Synthesis of Sulfonyl and Sulfenyl Derivatives of Pyridine and 1,2,4-Triazole", Russian Journal of Organic Chemistry, 2006, 42(6):918-921.
Aranapakam, V. et al., "Synthesis and Structure—Activity Relationship of a-Sulfonylhydroxamic Acids as Novel, Orally Active Matrix Metalloproteinase Inhibitors for the treatment of Osteoarthritis", J. Med. Chem., 2003, 46:2361.
Aranapakam, V. et al., "Synthesis and Structure—Activity relationship of n-Substituted 4-Arylsulfonylpiperidine-4-hydroxamic Acids as Novel, Orally Active matrix Metalloproteinase Inhibitors for the treatment of Osteoarthritis", J. Med. Chem., 2003, 46:2376.
Aranapakam, V. et al., "Synthesis and Structure - Activity relationships of 4- alkynyloxy Phenyl Sulfanyl, Sulfinyl, and Sulfonyl Alkyl Hydroxamates as Tumor Necrosis Factor—a Converting Enzyme and Matrix Metalloproteinase Inhibitors", J. Med. Chem., 2004, 47:6255.
Arevalo-Martin, A. et al., "Therapeutic Action of Cannabinoids in a Murine model of Multiple Sclerosis", J. of Neuroscience, 2003, 23(7):2511.
Atwell, G. J. et al., "Relationships between Structure and Kinetics of Cyclization of 2-Aminoaryl Amides: Potential Prodrugs of Cyclization-Activated Aromatic Mustards," J. Med. Chem, 1994, 37:371-380.
Audouze, K. et al., "New series of morpholine and 1,4-oxazepane derivatives as dopamine D4 receptor ligands: Synthesis and 3D-QSAR model." J. Med. Chem, 2004, 47(12):3089-3104.
Bair, K. W et al., "(1-pyrenylmethyl) amino alcohols, a new class of antitumor DNA intercalators. Discovery and initial amine side chain structure-activity studies". J. Med. Chem., 1990, 33:2385-2393.
Baker, D. et al., "Cannabinoids control spasticity and tremor in a multiple sclerosis model", Nature, 2000, 404:84.
Baltzly, R. et al., "The preparation of N-mono-substituted and unsymmetrically disubstituted piperazines". J. Am. Chem. Soc., 1944, 66:263-265.
Baltzly, R. et al., "Unsymmetrically substituted piperazines. V. Piperazine ureas", The Journal of the American Chemical Society, 1954, 76:1165-1166.
Balzarini, J. et al., "Antiretroviral activity of semisynthetic derivatives of glycopeptide antibiotics". J. Med. Chem., 2003, 46(13):2755-2764.
Beilstein Database—Beilstein Registry No. 1084348. CAS Registry No. 6125-38-8, dated Sep. 1, 2010.
Beilstein Database—Beilstein Registry No. 1179643. CAS Registry No. 54890-73-2, dated Sep. 1, 2010.
Beilstein Database—Beilstein Registry No. 5396840. CAS Registry No. 54890-82-3, dated Sep. 1, 2010.
Beilstein Database—Beilstein Registry No. 5398283. CAS Registry No. 68558-02-01, dated Sep. 1, 2010.
Beilstein Database—Beilstein Registry No. 857451. CAS Registry No. 37901-58-9, dated Sep. 1, 2010.
Binisti, C. et al., "Structure-Activity relationships in platelet-activating factor (PAF). 11-From PAF-antagonism to phospholipase A2 inhibition: syntheses and structure-activity relationships in 1-arylsulfamido-2-alkylpiperazines", Eur. J. Med. Chem., 2001, 36:809.
Brown. P. J. et al., "A ureido-thioisobutyric acid (GW9578) is a subtype-selective PPARalpha agonist with potent lipid-lowering activity", J. Med. Chem., 1999, 42(19):3785-3788.
Bruche, L. et al., "1,3-Dipolar cycloadditions of 3,5-dichloro-2,4,6-trimethylbenzonitrile oxide to (phenylsulfonyl)allenes", J. Org. Chem., 1985, 50(17):3206-3208.
Buckley, N. E. et al., "Immunomodulation by cannabinoids is absent in mice deficient for the cannabinoid CB2 receptor", Eur. J. Pharmacology, 2000, 396(2-3):141-149.
CAplus Database—Accession No. 1967:454417, Kunieda et al., Chem. Pharm. Bull. vol. 15, No. 3, pp. 350-351 (1967). (Abstract Only).
CAplus Database—Accession No. 1976:58806; Retrieved on Jan. 2, 2009; Babayan, A.T. et al. "Intramolecular rearrangement of ammonium ylide formed by the splitting of substituted dihydroisoindolinium salts," Doklady Akademii Nauk Armyanskoi SSR (1975) Vo. 61, pp. 40-43. (Abstract Only).
CAplus Database—Accession No. 1990:497413; Zara-Kaczian, Acta Chimica Hungarica (1989), vol. 126, pp. 441-454. (Abstract Only).
CAplus Database—Accession No. 2000:500169; Retrieved on Jan. 2, 2009; Tommasi, R. A. et al. "AutoChem: automated solution-phase parallel synthesis and purification via HPLC," J. Combinatorial Chem. (2000) vol. 2, pp. 447-449. (Abstract Only).
CAplus Database—Accession No. 2000:98008; Retrieved on Jan. 2, 2009; Organ, M. G. and Dixon, C. E. "The preparation of amino-substituted biaryl libraries: the application of solid-supported reagents to streamline solution-phase synthesis," Biotech. Bioeng. (2000) vol. 71, pp. 71-77. (Abstract Only).
Carenzi, A, et al., "New Isoxazole Derivatives Provided with Antihypertensive Activity", Arzneimittelforschung, 1989, 39(6):642-646.
Cartwright, D., et al., "Abnormal Nucleophillic substitution in 3-trichloromethylpyridine, its N- oxide and 3,5-Bis (trichloromethyl)pyridine". Tetrahedron, Elsevier Science Publishers, Amsterdam, 1995, 51(47):12791-12796.
Catalano, A. et al., "Constrained analogues of tocainide as potent skeletal muscle sodium channel blockers towards the development of antimyotonic agents", European Journal of Medicinal Chemistry, 2008, 43(11):2535-2540.
Chang. M. Y et al., "Reaction of different α-sulfonyl acetamides with methyl acrylate", Tetrahedron, 2008, 58(25):5075-5080.
Chem Abstract—Accession No. 126:89390, Abstract of JP8311026, Kumaiai Chemical Industry Co., Nov. 26, 1996.
ChemAbstract: CAS Registry No. 246020-62-2 (STN Entry Date Nov. 3, 1999).
Chemabstracts, Ukraine. Order Nos. T6110295, T5962700, T5962703 abstract and "Enamine Screening Library", Jan. 1, 2009, Enamine, 23 Alexandra Matrosova Sl., 01103 Kiev, Ukraine.
ChemAbstracts: CAS Registry Nos. 693218-49-4 (STN Entry Date Jun. 15, 2004) and 402562-90-7 (STN Entry Date Mar. 22, 2002).
Chen, D. et al., "Preparation, Properties, and Synthetic Potentials of Novel Boronates in a Fluorous Version (Fluorous Boronates)", Organic Letters, 2002, 4(6):1003-1005.

(56) References Cited

OTHER PUBLICATIONS

Clark, N. G. et al., "The Fungicidal Activity of Substituted Acetanilides and Related Compounds", Biochemical Journal, 1953, 55(5):839-851.

Cockcroft, X.-L. et al., "Phthalazinones 2: Optimisation and synthesis of novel potent inhibitors of poly(ADP-ribose)polymerase", Bioorg Med Chem Lett., 2006, 16(4):1040-1044.

Conway "Solid Dosage Forms" in Pharmaceutical Manufacturing Handbook: Production and Processes, edited by Shayne Cox Gad 2008 John Wiley & Sons, Inc., pp. 235-265.

Database PubChem Substance, 2005, Retrieved online from to: http://www.ncbi.nlm.nih.gov/pcsubstance.

Day, Jr., R. A. and Blanchard, W. A., "Polarography of phenyl 2-thienyl and 2,2'-dithienyl ketones," J. Am. Chem. Soc., 1954, 76(4):1166-1167.

El-Hawash, S. A. M., et al., "Synthesis and invitro-Anticancer and Antimicrobial Evaluation of Some Novel Quinoxalines Derived from 3-Phenylquinoxaline-2(1 H)-thione", Arch. Pharm. Chem. Life Sci., 2006, 339(8):437-447.

Ermann, M. et al. "Discovery of a novel class of CB2 receptor agonists". Presented at the 14th SCI-RSC Medicinal Chemistry Symposium, Churchill College, Cambridge, UK, Sep. 23-26, 2007. (Abstract Only).

Ermann, M. et al. "Discovery of a novel class of CB2 receptor agonists". Presented at the Cambridge Healthcare institute's 15th International Molecular Medicine Tri-Conference, Moscone Convention Center, San Francisco, CA, USA. Mar. 25-28, 2008. (Abstract Only).

Ermann, M. et al., "Arylsulfonamide CB2 receptor agonists: SAR and optimization of CB2 selectivity", Bioorg Med Chem Lett., 2008, 18(5):1725-1729.

Evans, W. J. et al., "A Rearrangement of Carbamyl-sulphones and -sulphides", Journal of the Chemical Society, 1936, p. 329-331.

Faucher, A. M. et al., "Discovery of small-molecule inhibitors of the ATPase activity of human papillomavirus E1 helicase", J. Med. Chem., 2004, 47(1):18-21.

Field, L. et al. "Grignard Reagents of Sulfones. IV. Reactions with Nitriles, Esters and an Isocyanate," J. Am. Chem. Soc., 1956, 78(17):4389-4394.

Field, L., et al., "Methyl p-Tolyl Sulfone", Organic Syntheses, Coll. vol. 4, p. 674, 1963; vol. 38, p. 62, (1958).

Fringuelli, F. et al., "Solvent-Free Al(OTf)3-Catalyzed Aminolysis of 1,2-Epoxides by 2-Picolylamine: A Key Step in the Synthesis of Ionic Liquids". J. Org. Chem., 2004, 69(22):7745-7747.

Gao, M., et al. "Synthesis of new carbon-11 labeled benzoxazole derivatives for PET imaging of 5-HT3 receptor," Eur. J. Med. Chem., 2008, 43(7):1570-1574.

Garst, M., et al., "Hydroformylation of bisolefinic amine derivatives catalyzed by cobalt and rhodium," J. Org. Chem., 1981, 46(22):4433-4438.

Gavalda, S. et al. "N-Sulfonyl hydroxamate derivatives as inhibitors of class II fructose-1,6-diphosphate aldolase," Bioorg Med Chem Lett., 2005, 15(24):5375-5377.

Goldschmidt. St. et al., "Biphenyl derivatives II. Basic 4-Biphenyl Compounds", Recueil des Travaux Chimiques des Pays-Bas, 1950, 69(9):1109-1117.

Grothe, W. "Effect of Potassium Sulfhydrate, Potassium Cyanide, and Potassium Rhodanide on Chloroacetvlanilides," Archiv der Pharmazie (Weinheim), vol. 238, 1900, 600-614.

Guindon, J. and Hohmann, A. G., "Cannabinoid CB2 Receptors: A Therapeutic Target for the Treatment of Inflammatory and Neuropathic Pain", British Journal of Pharmacology, 2008, 153(2):319-334.

Hadjipavlou-Litina, D. et al., "Thiazolyl-N-Substituted Amides: A group of effective anti-inflammatory agents with potential for local anesthetic properties. Synthesis, Biological Evaluation, and a QSAR Approach", Drua Development Research, 1999, 48(2):53-60.

Hanus, L. et al., "HU-308: A specific agonist for CB2, a peripheral cannabinoid receptor", PNAS, 1999, 96(25):14228-14233.

Hauske, J. et al., "Design and Synthesis of Novel FKBP Inhibitors." Journal of Medicinal Chemistry, 1992, 35(23):4284-4296.

Herndon, J. L. et al., "Ketanserin analogues: structure-affinity relationships for 5-HT2 and 5-HT1C serotonin receptor binding". J. Med. Chem, 1992, 35(26):4903-4910.

Ho, B. et al., "Synthesis and structure-activity relationships of potential anticonvulsants based on 2-piperidinecarboxylic acid and related pharmacophores," Eur. J. Med. Chem., 2001, 36(3):265-286.

Huang, X. et al., "A Novel Synthesis of Sulfones via the 0.0-Diethylphosphorotellurite Ion-Assisted Coupling of Arenesulfonyl Chlorides with Active Halides", Synthetic Communications, 1990, 20(15):2291-2295.

Ibrahim, M. M. et al., "Activation of CB2 cannabinoid receptors by AM1241 inhibits experimental neuropathic pain: Pain inhibition by receptors not present in the CNS", PNAS, 2003, 100(18):10529-10533.

Iddon, B. et al., "Condensed thiophen ring systems. Part XVII. A new synthesis of 10H-indeno[1,2-b][1]benzothiophen", Journal of the Chemical Society. Perkin Transactions 1, Jan. 1, 1974, 21:2505-2508.

Iddon, B. et al., "Polyhalogenoaromatic compounds. Part 42. 13C N.m.r. spectra of polyhalogeno-pyridines and -pyrimidines", Journal of the Chemical Society, Perkin Transactions 1, 1980, pp. 1370-1380.

Igarashi, J. et al., "Improved synthesis of quinine alkaloids with the Teoc protective group", Tetrahedron Letters, 2005, 46(37):6381-6384.

International Search Report and Written Opinion for PCT/EP2014/060033 mailed Jul. 3, 2014.

Ishii, K. et al., "Smiles Rearrangement of 2-(1-Methyl-1 H-tetrazol-5-ylthio) acetamides and their Sulfonyl Derivatives", Chem. Pharm. Bull., 1991, 39(12):3331-3334.

Iwakubo, M. et al., "Design and synthesis of Rho kinase inhibitors (II)", Bioorg. Med. Chem., 2006, 15(1):350-364.

Jaggar, S. I. et al., "The anti-hyperalgesic actions of the cannabinoid anandamide and the putative CB2 receptor agonist palmitoylethanolamide in visceral and somatic inflammatory pain", Pain, 1998, 76(1-2):189-199. (Abstract Only).

Johansen et al., AMPA Receptor Agonists: Resolution, Configurational Assignment, and Pharmacology of (+)-(S)- and (−)-(R)-2-Amino-3-(3-Hydroxy-5-(2-Pyridyl) Isoxazol-4-yl)Propionic Acid (1-Py-AMPA); Chirality, New York, 1997, 9(3): 274-280.

Kano, S. et al., "Formation of Some Heterocycles through Ring Transformation of 1-Arylazetidin-2-ones", Heterocycles, Dec. 30, 1977, 8(1):411-416.

Katoh, A., et al., "Synthesis of 6-(Bromoacetyl)Amino-2,3-Dimorpholino-Quinoxaline and Application to a new Fluorescence Derivatization Reagent of Fatty Acids for the High-Performance Liquid Chromatographic Analysis", Heterocycles, 1999, 50(1):299.

Katz, L., et al., "Hydrazine Derivatives. II. Ortho-Mercapto-Pyridinecarbohydrazides", J. Org. Chem., 1954, 19(5):711-717.

Klein, T. W., et al., "The Cannabinoid system and immune modulation", J. Leukocyte Biology, 2003, 74(4):486-496.

Kolehmainen, E. et al., "α-Phenylsulfonyl-N-arylacetamides (α-phenylsulfonylacetanilides): 1H,13C and 15N NMR spectral characterization", Magnetic Resonance in Chemistry, 2000, 38(5):384-385.

Krutosikova, A. et al., "Furan derivatives. LV. Preparation of 5-aryl-2-furfuryl phenyl and 5- aryl-2-furfuryl 4-tolyl sulfones", Chernick Zvesti (Chemical Papers), 1974, 28(3):414-417.

Kulkarni, S.S. et al., "Design and synthesis of noncompetitive metabotropic glutamate receptor subtype 5 antagonists", Bioorg Med Chem Lett., 2006, 16(13):3371-3375.

Lambeng, N. et al., "Discovery of a Novel Piperidinyl-Sulfonyl Benzoic Ester, Active as CB1 Agonist" Poster. 231st ACS National Meeting, Atlanta, GA. Mar. 26-30, 2006.

Leberre, A. et al., "No. 150—Alpha-sulfocarboxylic acids and derivatives. V.—Acyclic sulfamoyl carboxyesters and carboxamides. 1,2-Thiazetidine 3-one 1,1-dioxides" Bulletin De La Societe Chimique De France, 1975, pp. 807-811.

Lesser, R. et al. "Uber das Homo—oxythionaphthene (4-Ketoisothiochromane". Berichte, 1923, pp. 1642-1648.

Li, S. et al., "The Synthesis and Preliminary Activity Assay In Vitro of Peptide-like Derivatives as APN Inhibitors." Archives of Pharmacal Research, 2008, 31(10):1231-1239.

(56) References Cited

OTHER PUBLICATIONS

Lutz, R. E. et al., "Antimalarials. Some piperazine derivatives", Journal of Organic Chemistry, 1947, 12(6):771-775.

Mahmoud, A. M. et al., "Synthesis and Biological Activity of Some new 2-(N-Substituted Carboxamidomethyl Thio)-Naphth[1,2-d]Oxazoles—Part V", J. Indian Chem. Soc., vol. LIX, May 1982, DD. 675-677.

Malan Jr., T. P., et al., "CB2 cannabinoid receptor-mediated peripheral antinociception", Pain, 2001, 93(3):239-245.

Markley, L. D., et al., "Antipicornavirus activity of substituted phenoxybenzenes and phenoxypyridines", J. Med. Chem., 1986, 29( )3:427-433.

Marx, I. E. et al., "Discovery of α-amidosulfones as potent and selective agonists of CB2: Synthesis, SAR, and pharmacokinetic properties", Bioorganic and Medicinal Chemistry Letters, 2009, 19(1):31-35.

Messinger, P., "Sulfones via Mannich bases" Archiv der Pharmazie, 1973, 306(8):603-610.

Miroshnikova, O.V. et al., "Structure-activity relationships in the series of eremomycin carboxamides", Journal of Antibiotics, 2000, 53(3):286-293.

Miyano, S, et al., "Kinetic Resolution of Racemic b-Hydroxy Amines by Enantioselective N-Oxide formation", Journal of Organic Chemistry, 1985, 50(22):4350-4360.

Mohler, et al., "Nonsteroidal tissue selective androgen receptor modulators: a promising class of clinical candidates", Expert Opinion of Therapeutic Patents; Nov. 15, 2005 (11):1565-1585.

Nackley, A. G., et al., "Selective activation of cannabinoid CB2 receptors suppresses spinal fos protein expression and pain behavior in a rat model of inflammation", Neuroscience, 2003, 119(3):747-757.

Pollard, C. B. et al., "Some amides of piperazines", Journal of American Chemical Society, 1953, 75(2):491.

Revesz, L. et al., "Novel CCR1 antagonists with oral activity in the mouse collagen induced arthritis", Bioorganic and Medicinal Chemistry Letters, 2005, 15(23):5160-5164.

Riether, D. "Discovery of a Novel Class of CB2 Receptor Agonists" Abstract of Presentation at the first International Conference devoted to studies of the CB2 cannabinoid receptor. Banff, Alberta, Canada, May 31-Jun. 3, 2007.

Sakuraba, S, et al., "Efficient asymmetric hydrogenation of a-amino ketone derivatives. A highly enantioselective synthesis of phenylephrine, levamisole, carnitine and propranolol". Chemical and Pharmaceutical Bulletin, Pharm. Society of Japan, 1995, 43(5):738-747.

Schafer, H. et al. "On the Synthesis of 4-aminoquinolines and -quinolinones-(2) from Anthranilonitrile", Journal for Practical Chemistry, 1979, 321(4):695-698.

Seidel M. C. et al., "Reaction of Substituted 2-Carbethoxyacetyl-aminopyridines and Similar Compounds with Triethyl Orthoformate and Zinc Chloride," J. Org. Chem., 1970, 35(5):1662-1664.

Sheehan, J.C. et al., "The Synthesis and Reactions of Some Substituted Beta-Lactams," J. Am. Chem. Soc., 1951, 73:1761-1765.

Silverman, Richard B., The Organic Chemistry of Drug Design and Drug Action, 2nd Edition, 2004, Elsevier, pp. 29-34.

Sisko, J. et al., "An investigation of imidazole and oxazole syntheses using aryl-substituted TosMIC reagents", The Journal of Organic Chemistry, Mar. 10, 2000, 65(5):1516-1624, ISSN: 022-3263, p. 1523, table 5,; compound 69.

Smith, S. R., et al., "The anti-inflammatory activities of cannabinoid receptor ligands in mouse peritonitis models", Eur. J. Pharmacology, 2001, 432:p. 107.

Stalberg et al. "Capillary Electrophoretic Separation of Basic Drugs Using Surface-Modified C8 Capillaries and Derivatized Cyclodextrins as Structural/Chiral Selectors." Chromatographia, 1995, 40(11/12):697-704.

STN results for Dorme et al., "Bulletin de la Societe Chimique de France"; 1959, 9:2582-2588.

Strating, J., et al. "Nucleophilic Additions to Bis-Tertiobutyl Sulfonyl Acetylene (Properties of the sulfonyl group XLIV)", Recueil, 1954, pp. 709-716.

Swanson, D. M. et al., "Identification and biological evaluation of 4-(3-trifluoromethylpyridin-2-y1)piperazine-1-carboxylic acid (5-trifluoromethylpyridin-2-yl)amide, a high affinity TRPV1 (VR1) vanilloid receptor antagonist", J. Med. Chem., 2005, 48:1857-1872.

Tegley, et al., "Discovery of novel hydroxy-thiazoles as HIF-alpha prolyl hydroxylase inhibitors: SAR, synthesis, and modeling evaluation," Bioorganic & Medicinal Chemistry Letters, Pergamon, Elsevier Science, GB, 2008, 18(14):3925-3928.

Todorova, T. R., et al."Ring-enlargement and ring-opening reactions of 1,2-thiazetidin-3-one 1,1,-dioxides with ammonia and primary amines as nucleophiles". Helvetica Chimica Acta, 1999, 82(3):354-371.

Trang, T. et al., "Pain and Poppies: The Good, the Bad, and the Ugly of Opioid Analgesics", J. Neurosci., 2015, 35(41):13879-13888.

Troeger, J. and Uhde, R., "Lieber sulfonirte buttersauren", J. Prakt. Chem., 1899, 59:320-349.

Tweit, R. C., et al., "Synthesis of Antimicrobial Nitroimidazolyl 2-Sulfides, -Sulfoxides, and -Sulfones", J. Med. Chem., 1973, 16:1161-1169.

Ueda, Y., et al., "Involvement of cannabinoid CB2 receptor-mediated response and efficacy of cannabinoid CB2 receptor inverse agonist, JTE-907, in cutaneous inflammation in mice", Eur. J. Pharmacol., 2005, 520(1-3):164-171.

Van Sickle, et al., "Identification and Functional Characterization of Brainstem Cannabinoid CB2 Receptors", Science, 2005, 310(5746):329-332.

Venkov, A.P. et al., "A new synthesis of 1,2,3,4-tetrahydro-2-methyl-4-phenylisoquinolines", Synthesis, 1990, 1990(3):253-255.

Vogtle, M. M. et al., "An efficient protocol for the solid-phase synthesis of malondiamides", Molecules, 2005, 10(12):1438-1445.

Walker, G.N. et al., "Synthesis of Varied Heterocyclic and Substituted Aryl Alkyl Secondary Amines, Related Schiff Bases, and Amides", Journal of Medicinal Chemistry, 1966, 9(4):624-630.

Wang, Y. et al., "Rapid and efficient synthesis of 1,2,4-oxadiazoles utilizing polymer-supported reagents under microwave heating", Organic Letters, Mar. 3, 2005, 7(5):925-928, ISSN: 1523-7060, p. 927, compounds; 14,15.

Watson, R. J., et al., "An enantioselective synthesis of sulphonamide hydroxamic acids as matrix metalloproteinase inhibitors", Tetrahedron Letters, 2002, 43(4):683-685.

Wei, Ling et al., "Solid-phase synthesis of FKBP12 inhibitors: N-sulfonyl and N-carbamoylprolyl/pipecolyl amides ", Bioorganic & Medicinal Chemistry Letters, 2002, 12 (10):1429-1433.

Wermuth, C. G., "The Practice of Medicinal Chemistry", 2008, Third Edition, Ch. 17, pp. 363-379.

White, J.D. et al., "Conversion of Carbamates to Amidosulfones and Amides. Synthesis of the [14C]-Labeled Antiobesity Agent Ro23-7637", Organic Letters, Apr. 17, 2002, 4(10):1803-1806.

Yang, G. et al., "Synthesis and bioactivity of novel triazolo [1,5-a]pyrimidine derivatives[3]", Heteroatom Chemistry, 2001, 12(6):491-496.

Yokoyama, M. et al., "A regioselective synthesis of 3,5-disubslituted isoxazoles". J. Chem. Soc. Perkin Trans. I, 1986, pp. 67-72.

Yordanova, K. et al. "New method for the synthesis of 2,4-disubslituted morpho-lines", Chem. Ber., 1982, 115:2635-2642.

Zhang, B. and Breslow, R., "Ester Hydrolysis by a Catalytic Cyclodextrin Dimer Enzyme Mimic with a Metallobipy Metallobipyridyl ridvl Linkina Group", J. Am. Chem. Soc., 1997, 119(7):1676-1681.

Zimmer, A. et al., "Increased mortality, hypoactivity, and hypoalgesia in cannabinoid CB1 receptor knockout mice", Proc. Natl. Acad. Sci. USA, 1999, 96(10):5780-5785.

Zindell, R. et al., "Discovery of a novel class of CB2 agonists". General Poster Session. The 235th ACS National Meeting, New Orleans, LA, USA. Apr. 6-10, 2008.

Office Action dated Mar. 22, 2010, from the European Patent Office for Application # 078132032.

Office Action mailed Jan. 13, 2012, for U.S. Appl. No. 12/882,328, filed Sep. 15, 2010.

(56) References Cited

OTHER PUBLICATIONS

Office Action mailed Jan. 27, 2012, for U.S. Appl. No. 12/741,260, filed Jun. 17, 2010.

\* cited by examiner

(CYANO-DIMETHYL-METHYL)-ISOXAZOLES AND -[1,3,4]THIADIAZOLES

CROSS-REFERENCE TO RELATED APPLICATIONS

This application is a continuation of U.S. patent application Ser. No. 17/398,155, filed Aug. 10, 2021, which is a continuation of U.S. patent application Ser. No. 16/749,412, filed Jan. 22, 2020, now U.S. Pat. No. 11,084,810, which is a continuation of U.S. patent application Ser. No. 16/143,523, filed Sep. 27, 2018, now U.S. Pat. No. 10,570,125, which is a continuation of U.S. patent application Ser. No. 15/491,035, filed Apr. 19, 2017, now U.S. Pat. No. 10,112,934, which is a continuation of U.S. patent application Ser. No. 14/891,051, filed on Nov. 13, 2015, now U.S. Pat. No. 9,650,370, which is a national stage application of International (PCT) Patent Application Serial No. PCT/EP2014/060033, filed May 16, 2014, which claims the benefit of and priority to European Patent Application No. 13168165.2, filed on May 17, 2013; the entire contents of these applications are incorporated herein by reference in their entirety.

FIELD OF THE INVENTION

This invention relates to novel (Cyano-dimethyl-methyl)-isoxazoles- and -[1,3,4]thiadiazoles and their use as cannabinoid receptor 2 agonists (CB2 receptor agonists), pharmaceutical compositions containing the same, and methods of using the same as agents for the treatment of CB2 receptor mediated disorders or conditions.

BACKGROUND OF THE INVENTION

WO2008014199 and WO2008039645 discuss the CB2 receptor, and the therapeutic uses of the CB2 receptor agonist compounds disclosed therein. Further supporting evidence has more recently emerged in which the expression of CB2 in dorsal root ganglion neurons has been demonstrated in multiple species (Anand et al., 2008 Pain 138: 667-680). Neuronal expression of CB2 has been shown to be altered under pathological pain conditions suggesting a key role for CB2 neuronal signalling. A role for centrally located CB2 has been suggested by recent reports of an effect of CB2 on addictive behaviour (Xi et al., Nat. Neuroscience 2012, 14, 1160-1166; Morales & Bonci et al., Nature Med. 2012, 18, 504-505; Aracil-Fernandez et al., Neuropsychopharmacology 2012, 37, 1749-1763) and other conditions in which maladaptive impulsivity plays a role (Navarrete et al., Br. J. Pharmacol. 2012, 165, 260-273). A role of the hepatic CB2 in the pathogenesis of steatohepatitis and fibrotic liver diseases has also been suggested by several preclinical studies (Munoz-Luque et al., JPET 2008, 324, 475-483; Reichenbach et al., JPET 2012, 340, 629-637, WO2011009883). It is believed that the highly selective activation of the CB2 receptor with an agonist may offer avenues of harnessing the beneficial effects while avoiding the adverse effects seen with dual CB1/CB2 cannabinoid receptor agonists (see e.g. Expert Opinion on Investigational Drugs 2005, 14, 695-703). It is desirable therefore to provide agonists of CB2 with minimized CB1 activity.

WO2010036630, WO2010147792 and WO2010077836 disclose CB2 receptor agonists that are structurally closest to the compounds of the present invention.

DETAILED DESCRIPTION OF THE INVENTION

The present invention provides novel (Cyano-dimethyl-methyl)-isoxazoles and -[1,3,4]thiadiazoles, namely

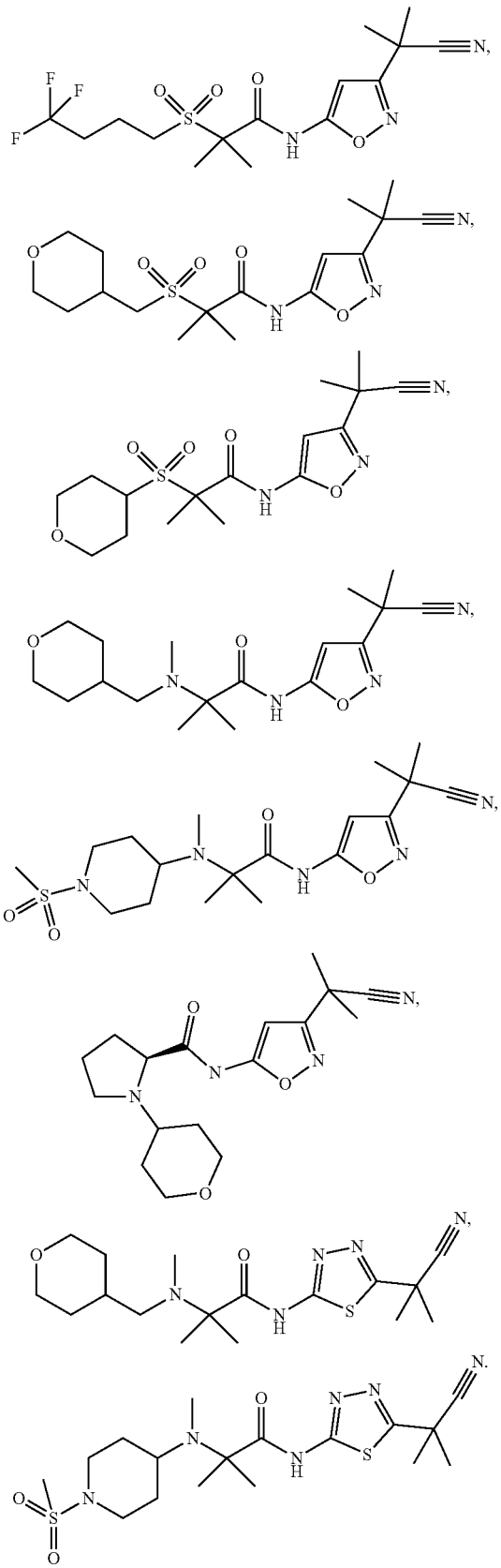

or a pharmaceutically acceptable salt thereof.

Compounds of the present invention are CB2 receptor agonists. The disclosed compounds are not only potent activators of the CB2 receptor (assay 1) but also show
1) no or low activation of the CB1 receptor (assay 2), and
2) no or low MDCK efflux (assay 3).

Thus, the present invention provides compounds which show a combination of potency as CB2 receptor agonists, high selectivity against the CB1 receptor, and low MDCK efflux.

It is demonstrated that the structurally closest compounds exemplified in WO2010036630, WO2010147792 and WO2010077836 do not have this balanced profile of desirable properties. The compounds of the present invention are therefore less likely to cause CB1 mediated side effects in vivo and to demonstrate in vivo efflux as compared to the closest prior art compounds, while they are expected to be efficacious in various in vivo models. Thus, they are expected to have a higher tolerability and are therefore potentially more viable for human use.

General Definitions

Terms not specifically defined herein should be given the meanings that would be given to them by one skilled in the art in light of the disclosure and the context.

Stereochemistry/Solvates/Hydrates

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-di-chloro-acetic acid, adipic acid, alginic acid, ascorbic acid, L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethane-sulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, Salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., 1977, 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

Biological Assays

The biological activity of compounds was determined by the following methods.

A. In Vitro Testing of CB2 Potency: CB2 cAMP (Assay 1)

CHO cells expressing human CB2R (Euroscreen) were plated at a density of 10,000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

B. In Vitro Testing of CB1 Potency: CB1 cAMP (Assay 2)

CHO cells expressing human CB1R (Euroscreen) were plated at a density of 10,000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

C. Assessment of Efflux in Madin-Darby Canine Kidney Cells Transfected with the Human MDR1 Gene (MDCK Assay) (Assay 3)

Apparent permeability coefficients (PE) of the compounds across the MDCK-MDR1 cell monolayers are measured (pH 7.4, 37° C.) in apical-to-basal (AB) and basal-to-apical (BA) transport direction. AB permeability (PEAB) represents drug absorption from the blood into the brain and BA permeability (PEBA) drug efflux from the brain back into the blood via both passive permeability as well as active transport mechanisms mediated by efflux and uptake transporters that are expressed on the MDCK-MDR1 cells, predominantly by the overexpressed human MDR1 P-gp. The compounds are assigned to permeability/absorption classes by comparison of the AB permeabilities with the AB permeabilities of reference compounds with known in vitro permeability and oral absorption in the human. Identical or similar permeabilities in both transport directions indicate passive permeation, vectorial permeability points to additional active transport mechanisms. Higher PEBA than PEAB indicates the involvement of active efflux mediated by MDR1 P-gp. Active transport is concentration-dependently saturable. MDCK-MDR1 cells (1-2×10e5 cells/1 cm2 area) are seeded on filter inserts (Costar transwell polycarbonate or PET filters, 0.4 μm pore size) and cultured (DMEM) for 7 days. Subsequently, the MDR1 expression is boosted by culturing the cells with 5 mM sodium butyrate in full medium for 2 days. Compounds are dissolved in appropriate solvent (like DMSO, 1-20 mM stock solutions). Stock solutions are diluted with HTP-4 buffer (128.13 mM NaCl, 5.36 mM KCl, 1 mM $MgSO_4$, 1.8 mM $CaCl_2$, 4.17 mM $NaHCO_3$, 1.19 mM $Na_2HPO_4 \times 7H_2O$, 0.41 mM $NaH_2PO_4 \times H_2O$, 15 mM HEPES, 20 mM glucose, 0.25% BSA, pH 7.4) to prepare the transport solutions (0.1-300 μM compound, final DMSO<=0.5%). The transport solution (TL) is applied to the apical or basolateral donor side for measuring A-B or B-A permeability (3 filter replicates), respectively. The receiver side contains the same buffer as the donor side. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution.

Biological Data

TABLE 1

Biological data of the compounds of the present invention in relation to the structurally closest prior art compounds as obtained in assays 1, 2 and 3.

| Example | Structure | CB2 $EC_{50}$ [nM] | CB1 $IC_{50}$ [nM] | MDCK efflux ratio (BA/AB) |
|---|---|---|---|---|
| Example 1 | 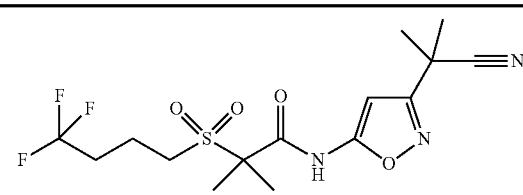 | 18 | 104,000 | 2.2 |
| Example 7 in WO2010036630 | 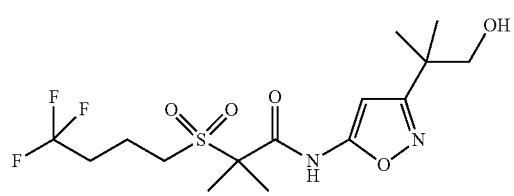 [SMILES: CC(C)(CO)c1cc(NC(=O)C(C)(C)S(=O)(=O)CCCC(F)(F)F)on1] | 15 | 28,000 | 6.9 |
| Example 134 in WO2010036630 | 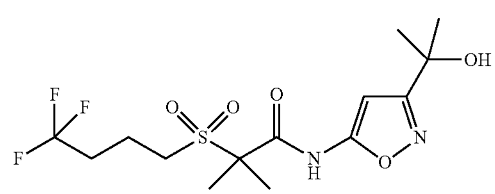 [SMILES: CC(C)(O)c1cc(NC(=O)C(C)(C)S(=O)(=O)CCCC(F)(F)F)on1] | 49 | 26,000 | 3.2 |
| Example 2 | 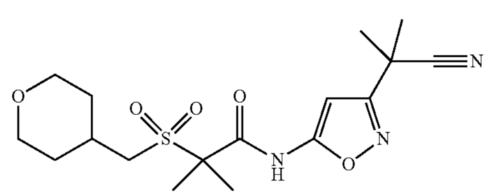 [SMILES: CC(C)(C#N)c1cc(NC(=O)C(C)(C)S(=O)(=O)CC2CCOCC2)on1] | 104 | >200,000 | 6.5 |

TABLE 1-continued

Biological data of the compounds of the present invention in relation to the structurally closest prior art compounds as obtained in assays 1, 2 and 3.

| Example | Structure | CB2 EC$_{50}$ [nM] | CB1 IC$_{50}$ [nM] | MDCK efflux ratio (BA/AB) |
| --- | --- | --- | --- | --- |
| Example 1 in WO2010036630 | 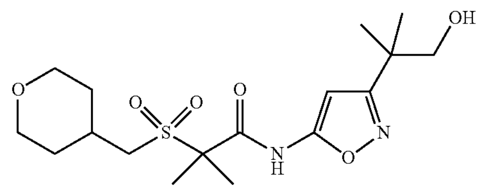 [SMILES: CC(C)(CO)c1cc(NC(=O)C(C)(C)S(=O)(=O)CC2CCOCC2)on1] | 88 | >50,000 | 16 |
| Example 17 in WO2010036630 | 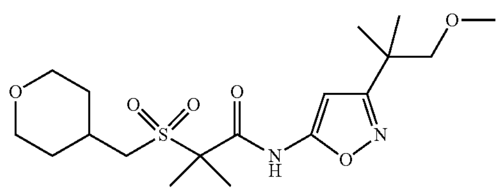 [SMILES: COCC(C)(C)c1cc(NC(=O)C(C)(C)S(=O)(=O)CC2CCOCC2)on1] | 30 | 8,600 | 4.8 |
| Example 3 | 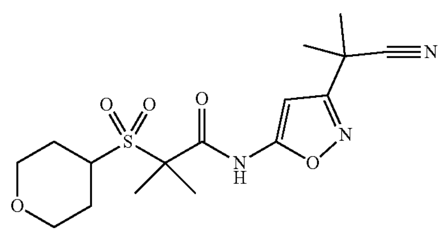 [SMILES: CC(C)(C#N)c1cc(NC(=O)C(C)(C)S(=O)(=O)C2CCOCC2)on1] | 8 | >200,000 | 2.5 |
| Example 2 in WO2010036630 | 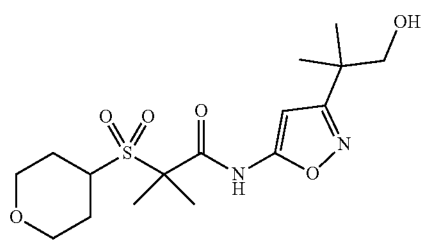 [SMILES: CC(C)(CO)c1cc(NC(=O)C(C)(C)S(=O)(=O)C2CCOCC2)on1] | 11 | 150,000 | 7.4 |
| Example 38 in WO2010036630 | 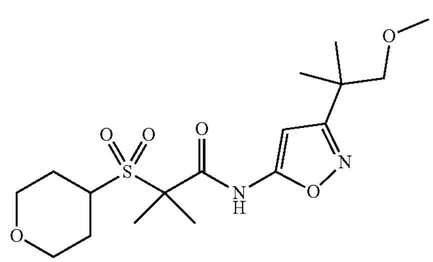 [SMILES: COCC(C)(C)c1cc(NC(=O)C(C)(C)S(=O)(=O)C2CCOCC2)on1] | 3.1 | 50,000 | 2.3 |
| Example 133 WO2010036630 | 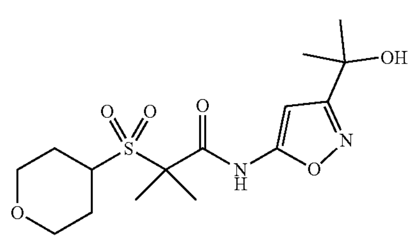 [SMILES: CC(C)(O)c1cc(NC(=O)C(C)(C)S(=O)(=O)C2CCOCC2)on1] | 140 | >200,000 | 4.7 |

TABLE 1-continued

Biological data of the compounds of the present invention in relation to the structurally closest prior art compounds as obtained in assays 1, 2 and 3.

| Example | Structure | CB2 EC$_{50}$ [nM] | CB1 IC$_{50}$ [nM] | MDCK efflux ratio (BA/AB) |
|---|---|---|---|---|
| Example 4 | 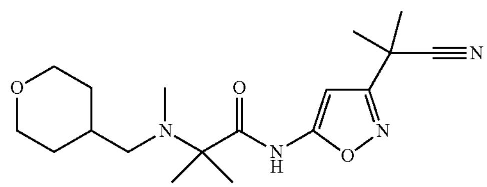 [SMILES: CN(CC1CCOCC1)C(C)(C)C(=O)Nc1cc(C(C)(C)C#N)no1] | 0.36 | 39,400 | 0.75 |
| Example 46 in WO2010147792 | 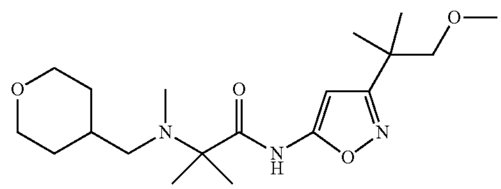 [SMILES: COCC(C)(C)c1cc(NC(=O)C(C)(C)N(C)CC2CCOCC2)on1] | 0.27 | 923 | 0.63 |
| Example 7 in WO2010147792 | 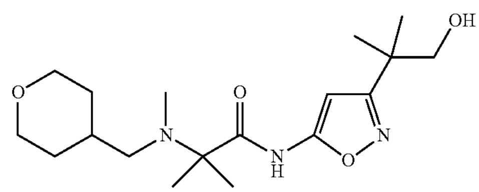 [SMILES: CN(CC1CCOCC1)C(C)(C)C(=O)Nc1cc(C(C)(C)CO)no1] | 0.68 | 8,082 | 1.2 |
| Example 5 | 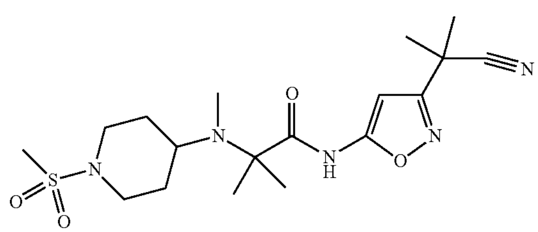 [SMILES: CN(C1CCN(S(C)(=O)=O)CC1)C(C)(C)C(=O)Nc1cc(C(C)(C)C#N)no1] | 0.23 | 2,500 | 5.1 |
| Example 47 in WO2010147792 | 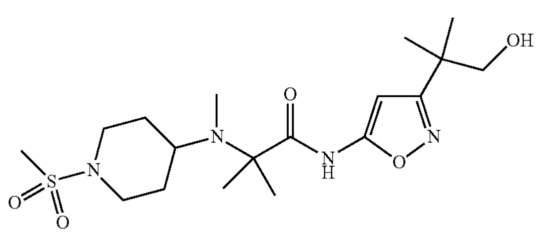 [SMILES: CN(C1CCN(S(C)(=O)=O)CC1)C(C)(C)C(=O)Nc1cc(C(C)(C)CO)no1] | 0.85 | 3,100 | 14 |
| Example 6 | 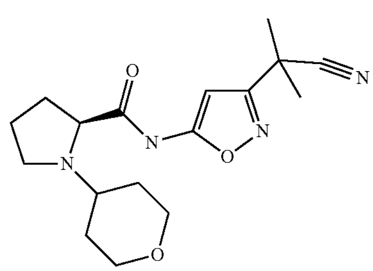 [SMILES: CC(C)(C#N)c1cc(NC(=O)[C@@H]2CCCN2C2CCOCC2)on1] | 11 | 87,000 | 1.0 |

TABLE 1-continued

Biological data of the compounds of the present invention in relation to the structurally closest prior art compounds as obtained in assays 1, 2 and 3.

| Example | Structure | CB2 EC$_{50}$ [nM] | CB1 IC$_{50}$ [nM] | MDCK efflux ratio (BA/AB) |
|---|---|---|---|---|
| Example 190 in WO2010077836 | 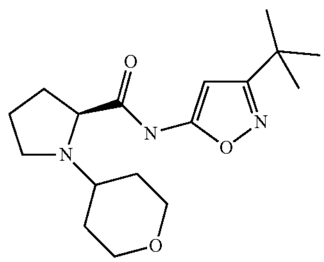 [SMILES: CC(C)(C)c1cc(NC(=O)[C@@H]2CCCN2C2CCOCC2)on1] | 2.8 | 7,870 | No data |
| Example 7 | 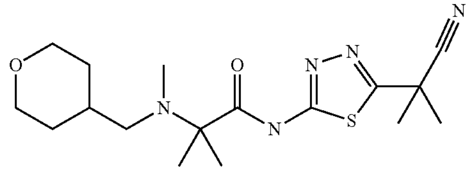 [SMILES: CN(CC1CCOCC1)C(C)(C)C(=O)Nc1nnc(C(C)(C)C#N)s1] | 25 | >200,000 | 2.1 |
| Example 30 in WO2010147792 | 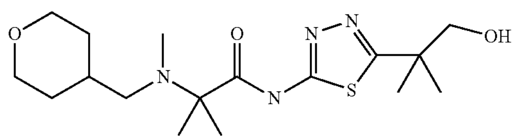 [SMILES: CN(CC1CCOCC1)C(C)(C)C(=O)Nc1nnc(C(C)(C)CO)s1] | 5.4 | 120,000 | 5.2 |
| Example 8 | 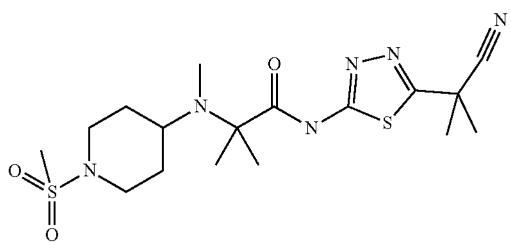 [SMILES: CN(C1CCN(S(C)(=O)=O)CC1)C(C)(C)C(=O)Nc1nnc(C(C)(C)C#N)s1] | 4.3 | 69,000 | 16 |

Table 1 shows a direct comparison of the relevant biological properties of compounds of the present invention with those of the closest prior art disclosed in WO 2010036630, WO 2010147792 and WO 2010077836 when assessed in assays 1, 2 and 3. Data demonstrate that compounds of the present invention have a more balanced profile in terms of CB2 potency, CB1 activity and MDCK efflux.

Method of Treatment

The present invention is directed to compounds which are useful in the treatment and/or prevention of a disease, disorder and/or condition wherein the activation of cannabinoid receptor 2 is of therapeutic benefit, including but not limited to the treatment and/or prevention of pain; inflammatory diseases and/or associated conditions; and psychiatric disorders and/or associated conditions.

In view of their pharmacological effect, the substances are suitable for the treatment of a disease or condition selected from the list consisting of (1) acute pain such as for example toothache, peri- and post-operative pain, traumatic pain, muscle pain, the pain caused by burns, sunburn, trigeminal neuralgia, pain caused by colic, as well as spasms of the gastro-intestinal tract or uterus; sprains;

(2) visceral pain such as for example chronic pelvic pain, gynaecological pain, pain before and during menstruation, pain caused by pancreatitis, peptic ulcers, interstitial cystitis, renal colic, cholecystitis, prostatitis, angina pectoris, pain caused by irritable bowel, non-ulcerative dyspepsia and gastritis, prostatitis, non-cardiac thoracic pain and pain caused by myocardial ischaemia and cardiac infarct;

(3) neuropathic pain such as low back pain, hip pain, leg pain, non-herpetic neuralgia, post herpetic neuralgia, diabetic neuropathy, lumbosacral radiculopathy, nerve injury-induced pain, acquired immune deficiency syndrome (AIDS) related neuropathic pain, head trauma, toxin and chemotherapy caused nerve injuries, phantom limb pain, multiple sclerosis, root avulsions, painful traumatic mononeuropathy, painful polyneuropathy, thalamic pain syndrome, post-stroke pain, central nervous system injury, post surgical pain, carpal tunnel syndrome, trigeminal neuralgia, post mastectomy syndrome, postthoracotomy syndrome, stump pain, repetitive motion pain, neuropathic pain associated hyperalgesia and allodynia, alcoholism and other drug-induced pain;

(4) inflammatory/pain receptor-mediated pain in connection with diseases such as for example osteoarthritis, rheumatoid arthritis, inflammatory arthropathy, rheumatic fever, tendo-synovitis, bursitis, tendonitis, gout and gout-arthritis, traumatic arthritis, vulvodynia, damage to and diseases of the muscles and fascia, juvenile arthritis, spondylitis, psoriasis-arthritis, myositides, dental disease, influenza and other viral infections such as colds, systemic lupus erythematodes or pain caused by burns;

(5) tumour pain associated with cancers such as for example lymphatic or myeloid leukaemia, Hodgkin's disease, non-Hodgkin's lymphomas, lymphogranulomatosis, lymphosarcomas, solid malignant tumours and extensive metastases;

(6) headache diseases of various origins, such as for example cluster headaches, migraine (with or without aura) and tension headaches;

(7) sympathetically maintained pain like complex regional pain syndrome Type I and II;

(8) painful conditions of mixed origin, such as for example chronic back pain including lumbago, or fibromyalgia, sciatica, endometriosis, kidney stones;

(9) inflammatory and/or oedematous diseases of the skin and mucous membranes, such as for example allergic and non-allergic dermatitis, atopic dermatitis, psoriasis, burns, sunburn, bacterial inflammations, irritations and inflammations triggered by chemical or natural substances (plants, insects, insect bites), itching; inflammation of the gums, oedema following trauma caused by burns, angiooedema or uveitis;

(10) Vascular and heart diseases which are inflammation-related like artheriosclerosis including cardiac transplant atherosclerosis, panarteritis nodosa, periarteritis nodosa, arteritis temporalis, Wegner granulomatosis, giant cell arthritis, reperfusion injury and erythema nodosum, thrombosis (e.g. deep vein thrombosis, renal, hepatic, portal vein thrombosis); coronary artery disease, aneurysm, vascular rejection, myocardial infarction, embolism, stroke, thrombosis including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries, artery restenosis;

(11) inflammatory changes connected with diseases of the airways and lungs such as bronchial asthma, including allergic asthma (atopic and non-atopic) as well as bronchospasm on exertion, occupationally induced asthma, viral or bacterial exacerbation of an existing asthma and other non-allergically induced asthmatic diseases; chronic bronchitis and chronic obstructive pulmonary disease (COPD) including pulmonary emphysema, viral or bacterial exacerbation of chronic bronchitis or chronic obstructive bronchitis, acute adult respiratory distress syndrome (ARDS), bronchitis, lung inflammation, allergic rhinitis (seasonal and all year round) vasomotor rhinitis and diseases caused by dust in the lungs such as aluminosis, anthracosis, asbestosis, chalicosis, siderosis, silicosis, tabacosis and byssinosis, exogenous allergic alveolitis, pulmonary fibrosis, bronchiectasis, pulmonary diseases in alpha1-antitrypsin deficiency and cough;

(12) inflammatory diseases of the gastrointestinal tract including Crohn's disease and ulcerative colitis, irritable bowel syndrome, pancreatitis;

(13) inflammation associated diseases of ear, nose, mouth and throat like influenza and viral/bacterial infections such as the common cold, allergic rhinitis (seasonal and perennial), pharyngitis, tonsillitis, gingivitis, laryngitis, sinusitis, and vasomotor rhinitis, fever, hay fever, thyroiditis, otitis, dental conditions like toothache, perioperative and post-operative conditions, trigeminal neuralgia, uveitis; iritis, allergic keratitis, conjunctivitis, blepharitis, neuritis nervi optici, choroiditis, glaucoma and sympathetic opthalmia, as well as pain thereof;

(14) diabetes mellitus and its comorbidities/effects/complications (such as diabetic vasculopathy, hypertension, dyslipidemia, diabetic neuropathy, cardiomyopathy, diabetic retinopathy, eye disease, diabetic nephropathy, liver disease) and diabetic symptoms of insulitis (for example hyperglycaemia, diuresis, proteinuria and increased renal excretion of nitrite and kallikrein); and orthostatic hypotension;

(15) sepsis and septic shock after bacterial infections or after trauma;

(16) inflammatory diseases of the joints and connective tissue such as vascular diseases of the connective tissue, sprains and fractures, and musculoskeletal diseases with inflammatory symptoms such as acute rheumatic fever, polymyalgia rheumatica, reactive arthritis, rheumatoid arthritis, spondylarthritis, and also osteoarthritis, and inflammation of the connective tissue of other origins, and collagenoses of all origins such as systemic lupus erythematodes, scleroderma, polymyositis, dermatomyositis, Sjögren syndrome, Still's disease or Felty syndrome; as well as vascular diseases such as panarteriitis nodosa, polyarthritis nodosa, periarteriitis nodosa, arteriitis temporalis, Wegner's granulomatosis, giant cell arteriitis, arteriosclerosis and erythema nodosum;

(17) diseases of and damage to the central nervous system such as for example cerebral oedema and the treatment and prevention of psychiatric diseases such as depression, for example, and for the treatment and prevention of epilepsy;

(18) disorders of the motility or spasms of respiratory, genito-urinary, gastro-intestinal including biliary or vascular structures and organs;

(19) post-operative fever;

(20) arteriosclerosis and related complaints;

(21) diseases of the genito-urinary tract such as for example urinary incontinence and related complaints, benign prostatic hyperplasia and hyperactive bladder, nephritis, cystitis (interstitial cystitis);

(22) morbid obesity and related complaints including sleep apnea, eating disorders and complications;

(23) neurological diseases such as cerebral oedema and angioedema, cerebral dementia like e.g. Parkinson's and Alzheimer's disease, senile dementia; multiple sclerosis, epilepsy, temporal lobe epilepsy, drug resistant epilepsy, stroke, myasthenia gravis, brain and meningeal infections like encephalomyelitis, meningitis, HIV as well as schizophrenia, delusional disorders, autism, affective disorders and tic disorders, Huntington's disease;

(24) cognitive impairments associated with schizophrenia, Alzheimer's Disease and other neurological and psychiatric disorders. With respect to Alzheimer's disease, the compounds of general formula (I) may also be useful as disease modifying agent;

(25) work-related diseases like pneumoconiosis, including aluminosis, anthracosis, asbestosis, chalicosis, ptilosis, siderosis, silicosis, tabacosis and byssinosis;

(26) various other disease states and conditions like epilepsy, septic shock e.g. as antihypovolemic and/or antihypotensive agents, sepsis, osteoporosis, benign prostatic hyperplasia and hyperactive bladder, nephritis, pruritis, vitiligo, disturbances of visceral motility at respiratory, genitourinary, gastrointestinal or vascular regions, wounds, allergic skin reactions, mixed-vascular and non-vascular syndromes, septic shock associated with bacterial infections or with trauma, central nervous system injury, tissue damage and postoperative fever, syndromes associated with itching;

(27) anxiety, depression, epilepsy, impulsivity, conditions in which maladaptive impulsivity plays a role, anorexia nervosa, binge eating, drug abuse (e.g. cocaine), alcohol abuse, nicotine abuse, borderline personality disorders, attention deficit and hyperactive disorders and neurodegenerative diseases such as dementia, Alzheimer's disease and Parkinson's disease. The treatment of affective disorders includes bipolar disorders, e.g. manic-depressive psychoses, extreme psychotic states, e.g. mania and excessive mood swings for which a behavioural stabilization is being sought. The treatment of anxiety states includes generalized anxiety as well as social anxiety, agoraphobia and those behavioural states characterized by social withdrawal, e.g. negative symptoms;

(28) diseases involving pathological vascular proliferation, e.g. angiogenesis, restenosis, smooth muscle proliferation, endothelial cell proliferation and new blood vessel sprouting or conditions requiring the activation of neovascularization. The angiogenic disease may for example be age-related macular degeneration or vascular proliferation associated with surgical procedures, e.g. angioplasty and AV shunts. Other possible uses are the treatments of arteriosclerosis, plaque neovascularization, hypertrophic cardiomyopathy, myocardial angiogenesis, valvular disease, myocardiac infarction, coronary collaterals, cerebral collaterals and ischemic limb angiogenesis;

(29) inflammatory and fibrotic liver diseases including insulin resistance, non-alcoholic steatohepatitis, liver cirrhosis, hepatocellular carcinoma, primary biliary cirrhosis, primary sclerosing cholangitis, alcoholic liver disease, drug-induced liver injury, viral hepatitis.

According to another embodiment, the compounds of the present invention are useful for the treatment and/or prevention of neuropathic pain.

Another aspect is the use of a compound of the present invention for the treatment and/or prevention of pain.

The present invention also relates to the use of the compounds for the treatment of neuropathic pain associated with a disease or condition selected from the list consisting of diabetic peripheral neuropathy, lumbosacral radiculopathy and post herpetic neuralgia.

A further aspect of the present invention is a method for the treatment and/or prevention of a disease or condition as mentioned above, which method comprises the administration of an effective amount of a compound of the present invention to a human being.

The present invention also relates to a compound of the invention as a medicament.

Furthermore, the present invention relates to the use of the compounds for the treatment and/or prevention of a disease, disorder or condition wherein the activation of the cannabinoid receptor 2 is of therapeutic benefit.

The dose range of the compounds of the invention applicable per day is usually from 1 to 1000 mg, preferably from 5 to 800 mg, more preferably from 25 to 500 mg. Each dosage unit may conveniently contain from 1 to 1000 mg, preferably 25 to 500 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Compositions

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) should be in the range from 0.1 to 95 wt.-%, preferably 5.0 to 90 wt.-% of the composition as a whole.

Suitable tablets may be obtained, for example, by mixing one or more compounds of the present invention with known excipients, for example inert diluents, carriers, disintegrants, adjuvants, surfactants, binders and/or lubricants. The tablets may also consist of several layers.

Combination Therapy

Compounds according to the present invention can be combined with other treatment options known to be used in the art in connection with a treatment of any of the indications the treatment of which is in the focus of the present invention.

Among such treatment options that are considered suitable for combination with the treatment according to the present inventions are:

non-steroidal antiinflammatory drugs (NSAIDs) including COX-2 inhibitors;
opiate receptor agonists;
Cannabinoid agonists or inhibitors of the endocannabinoid pathway
Somatostatin receptor agonists
Sodium channel blockers;
N-type calcium channel blockers;
serotonergic and noradrenergic modulators;
corticosteroids;
histamine H1, H2, H3 and H4 receptor antagonists;
proton pump inhibitors;
leukotriene antagonists and 5-lipoxygenase inhibitors;
local anesthetics;
VR1 agonists and antagonists;
Nicotinic acetylcholine receptor agonists;
P2X3 receptor antagonists;
NGF agonists and antagonists or anti-NGF antibodies;
NK1 and NK2 antagonists;
Bradykinin B1 antagonists
CCR2 antagonists
iNOS or nNOS or eNOS inhibitors
NMDA antagonist;
potassium channel modulators;
GABA modulators;
mGluR antagonists and modulators;
serotonergic and noradrenergic modulators;
anti-migraine drugs;

neuropathic pain drugs such as pregabaline or duloxetine; antidiabetic drugs and insulin.

In the following representative examples of such treatment options shall be given:

Non-steroidal antiinflammatory drugs (NSAIDs) including COX-2 inhibitors: propionic acid derivatives (alminoprofen, benoxaprofen, bucloxic acid, carprofen, fenhufen, fenoprofen, flubiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (meclofenamic acid, mefenamic acid, and tolfenamic acid), biphenyl-carboxylic acid derivatives, oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib) and the like;

Antiviral drugs like acyclovir, tenovir, pleconaril, peramivir, pocosanol and the like.

Antibiotic drugs like gentamicin, streptomycin, geldanamycin, doripenem, cephalexin, cefaclor, ceftazichine, cefepime, erythromycin, vancomycin, aztreonam, amoxicillin, bacitracin, enoxacin, mafenide, doxycycline, chloramphenicol and the like;

Opiate receptor agonists: morphine, propoxyphene (Darvon), tramadol, buprenorphin and the like;

Glucocorticosteroids such as bethamethasone, budesonide, dexamethasone, hydrocortisone, methylprednisolone, prednisolone, prednisone, triamcinolone and deflazacort; immunosuppressive, immunomodulatory, or cytsostatic drugs inlcuding but not limited to hydroxychlorquine, D-penicillamine, sulfasalizine, auranofin, gold mercaptopurine, tacrolimus, sirolimus, mycophenolate mofetil, cyclosporine, leflunomide, methotrexate, azathioprine, cyclophosphamide and glatiramer acetate and novantrone, fingolimod (FTY720), minocycline and thalidomide and the like;

anti-TNF antibodies or TNF-receptor antagonists such as but not limited to Etanercept, Infliximab, Adalimumab (D2E7), CDP 571, and Ro 45-2081 (Lenercept), or biologic agents directed against targets such as but not limited to CD-4, CTLA-4, LFA-1, IL-6, ICAM-1, C5 and Natalizumab and the like;

IL-1 receptor antagonists such as but not limited to Kineret;

Sodium channel blockers: carbamazepine, mexiletine, lamotrigine, tectin, lacosamide and the like.

N-type calcium channel blockers: Ziconotide and the like;

Serotonergic and noradrenergic modulators: paroxetine, duloxetine, clonidine, amitriptyline, citalopram;

Histamine H1 receptor antagonists: bromophtniramint, chlorpheniramine, dexchlorpheniramine, triprolidine, clemastine, diphenhydramine, diphenylpyraline, tripelennamine, hydroxyzine, methdiJazine, promethazine, trimeprazine, azatadine, cyproheptadine, antazoline, pheniramine pyrilamine, astemizole, terfenadine, loratadine, cetirizine, deslo-ratadine, fexofenadine and levocetirizine and the like;

Histamine H2 receptor antagonists: cimetidine, famotidine and ranitidine and the like;

Histamine H3 receptor antagonists: ciproxifan and the like

Histamine H4 receptor antagonists: thioperamide and the like

Proton pump inhibitors: omeprazole, pantoprazole and esomeprazole and the like;

Leukotriene antagonists and 5-lipoxygenase inhibitors: zafirlukast, mon-telukast, pranlukast and zileuton and the like;

Local anesthetics such as ambroxol, lidocaine and the like;

Potassium channel modulators, like retigabine;

GABA modulators: lacosamide, pregabalin, gabapentin and the like;

Anti-migraine drugs: sumatriptan, zolmitriptan, naratriptan, eletriptan, telcegepant and the like;

NGF antibodies such as RI-724 and the like;

Antidiabetic medication: Metformin, SUs, TZDs, GLP1 agonists, DPP4 inhibitor, SGLT2 inhibitor, insulin.

Combination therapy is also possible with new principles for the treatment of pain.

The combination of compounds is preferably a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased pharmacological effect, or some other beneficial effect of the combination compared with the individual components.

EXPERIMENTAL SECTION

List of Abbreviations

RT room temperature
BOC tert-butoxy-carbonyl-
EI-MS electron induced mass spectrometry
ESI-MS electrospray ionisation mass spectrometry
aq. aqueous
MS mass spectrum
MeOH methanol
EtOH ethanol
EE ethylacetate
DMF N,N-dimethylformamide
DCM dichloromethane
TBME tert-butylmethylether
THF tetrahydrofuran
Me-THF methyl-tetrahydrofuran
DIPEA N,N-diisopropyl ethylamine
HATU N,N,N',N'-tetramethyl-o-(7-azabenzotriazol-1-yl) uronium hexafluorophosphate
Rt retention time
d day(s)
sat. saturated
ACN acetonitrile
TFA trifluoroacetic acid
HPLC-Methods:
Method Name: A
Column: Xbridge C18, 4.6×30 mm, 3.5 μm
Column Supplier: Waters

| Gradient/Solvent Time [min] | % Sol [H₂O, 0.1% NH₃] | % Sol [ACN] | Flow [mL/min] | Temp [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

Method Name: B
Column: Sunfire C18, 2.1×30 mm, 2.5 μm
Column Supplier: Waters

| Gradient/Solvent Time [min] | % Sol [H₂O, 0.1% TFA] | % Sol [ACN] | Flow [mL/min] | Temp [° C.] |
|---|---|---|---|---|
| 0.0 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

Method Name: C
Column: XBridge C18, 4.6×30 mm, 3.5 μm
Column Supplier: Waters

| Gradient/Solvent Time [min] | % Sol [H₂O, 0.1% NH₃] | % Sol [Methanol] | Flow [mL/min] | Temp [° C.] |
|---|---|---|---|---|
| 0.0 | 95 | 5 | 4 | 60 |
| 0.15 | 95 | 5 | 4 | 60 |
| 1.7 | 0 | 100 | 4 | 60 |
| 2.1 | 0 | 100 | 4 | 60 |

Method Name: D
Column: StableBond C18, 4.6×30 mm, 3.5 μm
Column Supplier: Agilent

| Gradient/Solvent Time [min] | % Sol [H₂O, 0.1% TFA] | % Sol [Methanol] | Flow [mL/min] | Temp [° C.] |
|---|---|---|---|---|
| 0.0 | 95 | 5 | 4 | 60 |
| 0.15 | 95 | 5 | 4 | 60 |
| 1.7 | 0 | 100 | 4 | 60 |
| 2.1 | 0 | 100 | 4 | 60 |

Method Name: E
Column: XBridge C18, 4.6×30 mm, 3.5 μm
Column Supplier: Waters

| Gradient/Solvent Time [min] | % Sol [H₂O, 0.1% NH₃] | % Sol [ACN] | Flow [mL/min] | Temp [° C.] |
|---|---|---|---|---|
| 0.0 | 95 | 5 | 4 | 60 |
| 0.15 | 95 | 5 | 4 | 60 |
| 1.7 | 0 | 100 | 4 | 60 |
| 2.25 | 0 | 100 | 4 | 60 |

Method Name: F
Column: Sunfire C18, 3×30 mm, 2.5 μm
Column Supplier: Waters

| Gradient/Solvent Time [min] | % Sol [H₂O, 0.1% TFA] | % Sol [ACN] | Flow [mL/min] | Temp [° C.] |
|---|---|---|---|---|
| 0.0 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: G
Column: Sunfire C18, 4.6×30 mm, 3.5 μm
Column Supplier: Waters
Device description: Agilent 1100 with DAD, Waters Autosampler and MS-Detector

| Gradient/Solvent Time [min] | % Sol [H₂O, 0.1% TFA] | % Sol [ACN] | Flow [mL/min] | Temp [° C.] |
|---|---|---|---|---|
| 0.0 | 98 | 2 | 2.5 | 60 |
| 1.5 | 0 | 100 | 2.5 | 60 |
| 1.8 | 0 | 100 | 2.5 | 60 |

Method Name: H
Column: XBridge C18, 3.0×30 mm, 2.5 μm
Column Supplier: Waters
Device description: Waters Acquity with DA- and MS-Detector and CTC Autosampler

| Gradient/Solvent Time [min] | % Sol [H₂O, 0.1% NH₃] | % Sol [ACN] | Flow [mL/min] | Temp [° C.] |
|---|---|---|---|---|
| 0.0 | 98 | 2 | 2.0 | 60 |
| 1.2 | 0 | 100 | 2.0 | 60 |
| 1.4 | 0 | 100 | 2.0 | 60 |

Preparation of Intermediates

Intermediate 1:
2-Methyl-2-(tetrahydro-pyran-4-sulfonyl)-propionic acid

For additional analytical data: see WO2010036630

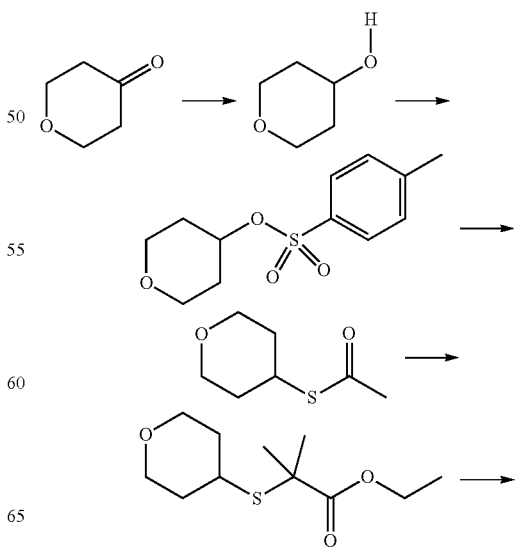

-continued

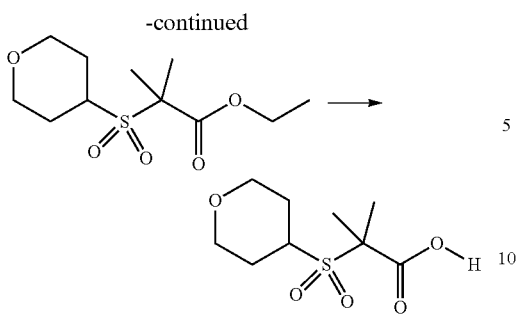

Step 1: Tetrahydropyran-4-ol

To 75 g (0.75 mol) of tetrahydropyran-4-one in THF (150 mL) is added a suspension of 28.4 g (0.75 mol) LiAlH₄ in THF (600 mL) under nitrogen atmosphere maintaining the temperature below 30° C. with the aid of an ice-bath. Then the reaction is allowed to warm to RT and stirred for 5 h. The reaction is quenched by addition of sat. aq. NH₄Cl solution until effervescence ceased. The resulting precipitate is removed by filtration through Celite® and washed with THF (150 mL). The filtrate is concentrated under reduced pressure to afford 71.1 g of tetrahydropyran-4-ol. Yield: 92%.

Step 2: Toluene-4-sulfonic acid tetrahydropyran-4-yl ester

To 133 g (1.31 mol) of tetrahydropyran-4-ol in pyridine (1.5 L) are added 373 g (1.95 mol) of p-toluenesulfonyl-chloride portionwise at 10° C. After complete addition the reaction is allowed to warm to RT and stirred for 18 h. The reaction is poured onto a stirred mixture of aq. HCl/ice. The resulting precipitate is isolated by filtration and dissolved in DCM (1 L). The organic layer is washed with 1 M aq. HCl solution (1 L), followed by sat. aq. NaHCO₃ solution (1 L) and is then dried over Na₂SO₄. Filtration and concentration of the filtrate under reduced pressure gives 300 g of toluene-4-sulfonic acid tetrahydropyran-4-yl ester. Yield: 90%; ESI-MS: 257 [M+H]⁺

Step 3: Thioacetic acid S-(tetrahydro-pyran-4-yl) ester

To 300 g (1.175 mol) of toluene-4-sulfonic acid tetrahydropyran-4-yl ester in DMF (3 L) are added 268 g (2.35 mol) potassium thioacetate, followed by a catalytic amount of NaI (0.12 g, 10 mol %) at RT. After complete addition, the reaction is heated to 50° C. for 20 h. The reaction mixture is partitioned between TBME (3 L) and water (3 L), the aq. layer is extracted with TBME (2 L), then saturated with NaCl and extracted again with TBME (2×2 L). The combined organic extracts are dried over Na₂SO₄, filtered and the solvent is removed under reduced pressure to afford 153 g of thioacetic acid S-(tetrahydro-pyran-4-yl) ester. Yield: 81%; ESI-MS: 161 [M+H]⁺

Step 4: 2-Methyl-2-(tetrahydro-pyran-4-ylsulfanyl)-propionic acid ethyl ester A solution of 153 g (0.96 mol) of thioacetic acid S-(tetrahydro-pyran-4-yl) ester in EtOH (3.5 L) is degassed with nitrogen over 0.5 h and 125 g (2.23 mol) of KOH are added. Then a solution of 250 mL (1.68 mol) of ethyl α-bromoisobutyrate in EtOH (1 L) are added over 0.5 h, during which the temperature increased to 40° C. The reaction is stirred for 18 h at RT under a nitrogen atmosphere. The reaction mixture is filtered, the solid is washed with EtOH (0.5 L) and the filtrate is concentrated under reduced pressure. The crude material is dryloaded onto silica and purified by dry-flash column chromatography (silica, eluent: nheptanes, 2-10% EE) to afford 158 g of 2-methyl-2-(tetrahydro-pyran-4-ylsulfanyl)-propionic acid ethyl ester. Yield: 71%; ESI-MS: 233 [M+H]⁺

Step 5: 2-Methyl-2-(tetrahydro-pyran-4-sulfonyl)-propionic acid ethyl ester

To 158 g (0.68 mol) of 2-methyl-2-(tetrahydro-pyran-4-ylsulfanyl)-propionic acid ethyl ester in dioxane/water (4/1, 1.6 L) are added 835 g (1.35 mol) of OXONE® in portions over 50 min. The reaction mixture is stirred at RT for 18 h. The solid is removed by filtration and washed with dioxane (1 L). The combined filtrates are concentrated under reduced pressure. The residue is dissolved in EE (1.5 L) and washed with water (1 L). The organic layer is dried over Na₂SO₄, filtered and the solvent is removed under reduced pressure to afford 166 g of 2-methyl-2-(tetrahydro-pyran-4-sulfonyl)-propionic acid ethyl ester. Yield: 92%; ESI-MS: 265 [M+H]⁺

Step 6: 2-Methyl-2-(tetrahydro-pyran-4-sulfonyl)-propionic acid

To 166 g (0.63 mol) of 2-methyl-2-(tetrahydro-pyran-4-sulfonyl)-propionic acid ethyl ester in THF/water (4/1, 1.66 L) are added 50.5 g (1.26 mol) of NaOH pellets in portions over 20 min. The reaction is stirred at RT for 2.5 d. The organic solvent is removed under reduced pressure and the aq. residue is diluted with water (2 L) and washed with DCM (2 L). The aq. layer is acidified to pH 1-2 with concentrated HCl and then extracted with DCM (3×2 L). The acidic aqueous layer is further saturated with NaCl and extracted again with DCM (6×2 L). The combined organic extracts are concentrated under reduced pressure to give 123 g of 2-methyl-2-(tetrahydro-pyran-4-sulfonyl)-propionic acid. Yield: 83%; ESI-MS: 235 [M+H]⁻

Intermediate 2: 2-Methyl-2-(tetrahydro-pyran-4-ylmethanesulfonyl)-propionic acid For additional analytical data: see WO2010036630

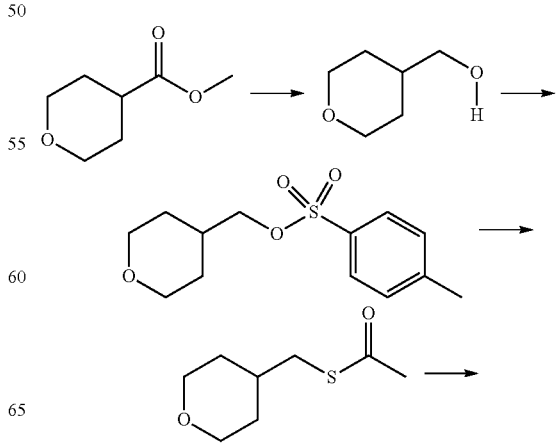

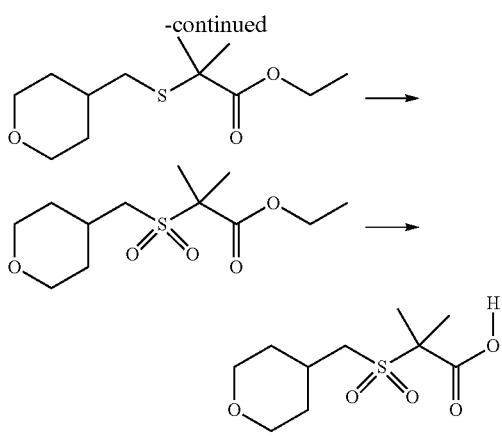

Step 1: (Tetrahydro-pyran-4-yl)-methanol

To 250 mL of LiAlH$_4$ (2.3 M solution in THF, 0.58 mol) in THF (200 mL) is added dropwise a solution of 130 mL (0.974 mol) of tetrahydro-pyran-4-carboxylic acid methyl ester in THF (900 mL) under nitrogen atmosphere. The temperature is kept at 40-45° C. with an ice-bath. Upon complete addition, the reaction is stirred at RT for 1.5 h. The reaction is cooled in an ice-bath and quenched with addition of water (22 mL), 15% aq. NaOH solution (21 mL) and water (66 mL). The resulting precipitate is removed by filtration through Celite® and is rinsed with THF (300 mL). The filtrate is concentrated under reduced pressure to afford 102.5 g of (tetrahydro-pyran-4-yl)-methanol. Yield: 91%

Step 2: Synthesis of toluene-4-sulfonic acid tetrahydro-pyran-4-ylmethyl ester Prepared as described by adaptation of the following literature reference: Radziszewski, J. G. et al. *J. Am. Chem. Soc.* 1993, 115, 8401.

To 97 g (810 mmol) of (tetrahydro-pyran-4-yl)-methanol in 2-methyltetrahydrofuran (190 mL) are added 165 mL of 50% aq. NaOH solution. To this stirred suspension is added dropwise with cooling a solution of p-toluene-sulfonylchloride (283 g, 1.46 mol) in 2-methyltetrahydrofuran (280 mL). The reaction is stirred at 30-35° C. for 18 h. The suspension is poured into a mixture of ice-water (280 mL) and aq. HCl solution (37%, 203 mL). After addition of methylcyclohexane (1.4 L) and further ice-water (0.2 L), the reaction mixture is stirred for 2 h in an ice-bath. The resulting crystalline precipitate is isolated by filtration and washed with methylcyclohexane (0.5 L) and water (0.5 L). Drying under reduced pressure at 40° C. gave 216 g of toluene-4-sulfonic acid tetrahydro-pyran-4-ylmethyl ester. Yield: 99%; ESI-MS: 271 [M+H]$^+$

Step 3: Thioacetic acid S-(tetrahydro-pyran-4-ylmethyl) ester

Prepared as described by adaptation of the following literature reference: Watson, R. J. et al. *Tetrahedron Lett.* 2002, 43, 683-685.

To 224 g (0.83 mol) of toluene-4-sulfonic acid tetrahydro-pyran-4-ylmethyl ester in methyl isobutylketone (1.6 L) are added 189 g (1.66 mol) of potassium thioacetate. The suspension is stirred at 70° C. for 4.5 h. The reaction mixture is cooled to RT and water (1.8 L) is added. The organic layer is washed with 10% aq. K$_2$CO$_3$ solution (1.8 L) and water (1 L). The organic layer is filtered through Celite® (20 g), activated charcoal (20 g) and Na$_2$SO$_4$ (20 g) and the filtrate is concentrated under reduced pressure. The residual oil is azeotroped with methylcyclohexane (200 mL) and n-heptanes (250 mL) to afford 138 g of thioacetic acid S-(tetrahydro-pyran-4-ylmethyl) ester. Yield: 96%; ESI-MS: 175 [M+H]$^+$

Step 4: 2-Methyl-2-(tetrahydro-pyran-4-ylmethanesulfonyl)-propionic acid ethyl ester A 90 g (516 mmol) of thioacetic acid S-(tetrahydro-pyran-4-ylmethyl) ester in toluene (500 mL) under nitrogen atmosphere is cooled in an ice-bath. A solution of sodium ethoxide in EtOH (21%, 231 mL) is added and the reaction stirred for 50 min. Then 76 mL (516 mmol) of ethyl α-bromoisobutyrate are added and the reaction stirred for 1 h. To the reaction mixture are added glacial acetic acid (8.9 mL) and water (500 mL). The organic layer is separated and washed with water (500 mL). A 3-neck round bottom flask is charged with water (500 mL), OOXONE® (477 g, 775 mmol) and tetrabutylammonium-hydrogensulfate (5 g, 15 mmol) and the organic layer is added. The reaction mixture is stirred for 2 d at RT. The solids are removed by filtration and the layers of the filtrate are separated. The organic layer is washed with water (2×500 mL). The solvent is removed under reduced pressure and further azeotroped with toluene to give 125 g of 2-methyl-2-(tetrahydropyran-4-ylmethanesulfonyl)-propionic acid ethyl ester. Yield: 87%; ES-MS: 279 [M+H]$^+$

Step 5: 2-Methyl-2-(tetrahydro-pyran-4-ylmethanesulfonyl)-propionic acid

To 123 g (0.44 mol) of 2-methyl-2-(tetrahydro-pyran-4-ylmethanesulfonyl)-propionic acid ethyl ester in THF (450 mL) are added 663 mL of 2M aq. NaOH solution (1.33 mol). The reaction is stirred at RT for 1 h. To the reaction mixture is added TBME (1.25 L) and the layers are separated. The aq. layer is cooled in an ice bath and then acidified with 37% aq. HCl solution (123 mL). The resulting precipitate is isolated by filtration, washed with water (200 mL) and dried under reduced pressure at 50° C. to afford 101 g of 2-methyl-2-(tetrahydro-pyran-4-ylmethanesulfonyl)-propionic acid. Yield: 91%; ESI-MS: 251 [M+H]$^+$

Intermediate 3: Synthesis of 2-Methyl-2-[methyl-(tetrahydro-pyran-4-ylmethyl)-amino]-propionic acid For additional analytical data: see WO2010036630

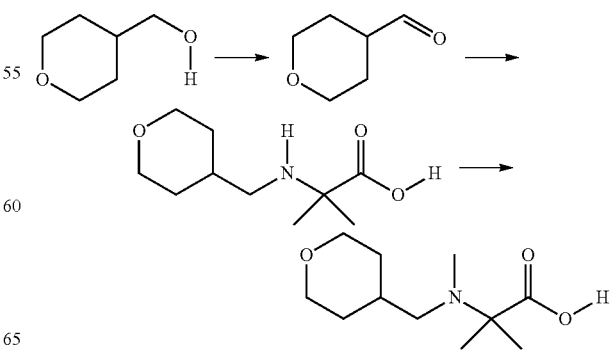

Step 1: Tetrahydro-pyran-4-carbaldehyde

To 5.00 g (43.0 mmol) of (tetrahydro-pyran-yl)-methanol in DCM (50 mL) are added 67 mg of 2,2,6,6-tetramethyl-1-piperidinyloxy (0.43 mmol), a solution of 9.04 g (108 mmol) NaHCO₃ in water (70 mL) and 512 mg (4.30 mmol) of potassium bromide at 20° C. The suspension is cooled in an ice bath to 4° C. Then a solution of 23.5 mL sodium hypochlorite (10-15% free chlorine; 47.4 mmol) is added in 35 min. The suspension is stirred for 30 min at 4-9° C. and further 45 min to reach 17° C. 4.80 mL sodium hypochlorite (10-15% free chlorine) is added within 15 min. The reaction is stirred for 16 h at RT. The suspension is filtered and the layers are separated. The aq. layer is washed with 50 mL DCM, the combined organic layers are washed with 50 mL water. The solvent is removed under reduced pressure to afford 3.00 g of tetrahydro-pyran-4-carbaldehyde. Yield: 61%; ESI-MS: 113 [M+H]⁻

Step 2: 2-Methyl-2-[(tetrahydro-pyran-4-ylmethyl)-amino]-propionic acid

To 0.90 g (8.76 mmol) of 2-amino-2-methyl-propionic in 10 mL MeOH is added at RT 1.00 g (8.76 mmol) of tetrahydro-pyran-4-carbaldehyde. After 25 min Pd(OH)₂ (310 mg, w=20%) is added. The reaction is stirred at 50° C. and 2757 kPa hydrogen pressure for 18 h. 10 mL of acetonitrile and 20 mL of water are added, filtered through celite to remove the catalyst and washed with water. The solvent is removed under reduced pressure to give 1.62 g of crude product, which is recrystallized from MeOH and water to afford 1.24 g of 2-methyl-2-[(tetrahydro-pyran-4-ylmethyl)-amino]-propionic acid. Yield: 70%; ESI-MS: 202 [M+H]⁺

Step 3: 2-Methyl-2-[methyl-(tetrahydro-pyran-4-ylmethyl)-amino]-propionic acid 1.00 g (4.97 mmol) of 2-methyl-2-[(tetrahydro-pyran-4-ylmethyl)-amino]-propionic acid is suspended in 20 mL of EtOH. 350 mg Pd(OH)₂ (0.50 mmol, w=20%) are added, followed by 0.74 mL of formaldehyde (9.88 mmol; 37% in water). The suspension is stirred for 24 h at 100° C. and 2916 kPa hydrogen pressure. The reaction mixture is filtered through celite and washed with EtOH. The solvent is removed under reduced pressure to afford 0.90 g of 2-methyl-2-[methyl-(tetrahydro-pyran-4-ylmethyl)-amino]-propionic acid. Yield: 84%; ESI-MS: 216 [M+H]⁺

Intermediate 4: Synthesis of 2-[(1-Methanesulfonyl-piperidin-4-yl)-methyl-amino]-2-methyl-propionic acid

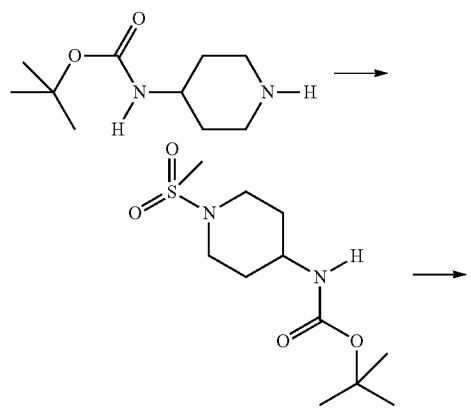

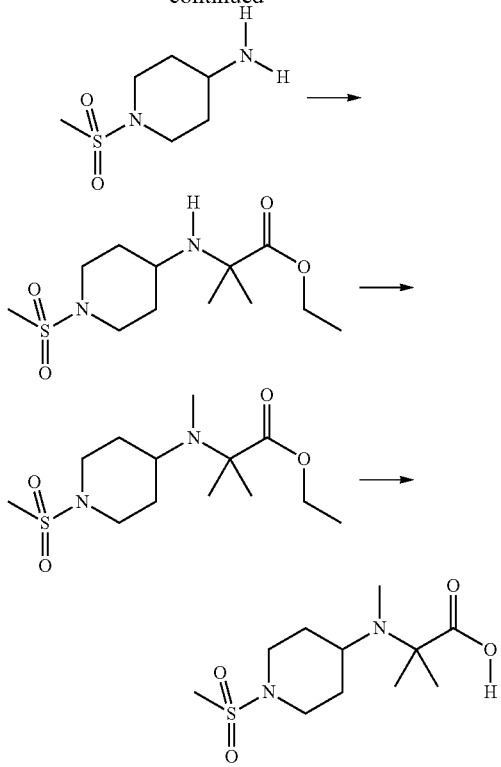

Step 1: (1-Methanesulfonyl-piperidin-4-yl)-carbamic acid tert-butyl ester 5.00 g (25.0 mmol) of BOC-4-aminopiperidine are dissolved in pyridine (19.8 mL) and cooled in an ice bath. 2.13 mL (27.5 mmol) of methanesulfonyl chloride are added slowly. The reaction is stirred at RT for 16 h. After diluting with water, the reaction is extracted with DCM. Organic layers are washed with water, dried with MgSO₄ and filtered. The solvent is removed under reduced pressure to afford 6.30 g of (1-Methanesulfonyl-piperidin-4-yl)-carbamic acid tert-butyl ester. Yield: 91%; ESI-MS: 279 [M+H]⁺

Step 2: 1-Methanesulfonyl-piperidin-4-ylamine 6.30 g (22.63 mmol) of (1-methanesulfonyl-piperidin-4-yl)-carbamic acid tert-butyl ester are dissolved in DCM (74 mL) and 17.4 mL (226 mmol) TFA are added. The reaction is stirred at RT for 16 h. The solvent is removed under reduced pressure. The crude product is diluted with diethylether at 40° C., the precipitate is filtered, washed with water and dried. The product is dissolved in MeOH, polymer supported hydrogencarbonate (PL-HCO₃ MP Resin, Agilent Technologies) is added and the suspension is stirred for a few minutes. The resin is filtered and the solvent is removed under reduced pressure to afford 4.00 g of 1-methanesulfonyl-piperidin-4-ylamine. Yield: 99%; ESI-MS: 179 [M+H]⁺; HPLC (Rt): 0.26 min (method E)

Step 3: 2-(1-Methanesulfonyl-piperidin-4-ylamino)-2-methyl-propionic acid ethyl ester 2.40 g (13.5 mmol) of 1-methanesulfonyl-piperidin-4-ylamine are dissolved in DMF (32.8 mL). 5.58 g (40.4 mmol) of K$_2$CO$_3$, 3.06 mL (20.2 mmol) ethyl-2-bromoisobutyrate and 1.12 g (6.73 mmol) of KI are added at RT. The reaction is stirred 16 h. Additional ethyl-2-bromoisobutyrate (3.06 mL) and KI (1.12 g) are added and the reaction mixture is stirred for further 16 h. Water and sat. aq. K$_2$CO$_3$ solution is added, the aqueous layer extracted with EE. The combined organic layers are dried over MgSO$_4$ and filtered. The solvent is removed under reduced pressure to afford the crude product, which is purified by silica gel chromatography (eluent: EE/MeOH 95/5) to afford 0.56 g of 2-(1-methanesulfonyl-piperidin-4-ylamino)-2-methyl-propionic acid ethyl ester. Yield: 14%; ESI-MS: 293 [M+H]$^+$; HPLC (Rt): 0.97 min (method E)

Step 4: 2-[(1-Methanesulfonyl-piperidin-4-yl)-methyl-amino]-2-methyl-propionic acid ethyl ester 0.71 g (2.43 mmol) of 2-(1-methynesulfonyl-piperidin-4-ylamino)-2-methyl-propionic acid ethyl ester are dissolved in DMF (5.92 mL). 1.51 g (10.9 mmol) K$_2$CO$_3$ and 227 µl (3.64 mmol) methyl iodide are added at RT. The reaction is stirred for 2 d. Additional methyl iodide (227 µl) is added an stirring is continued for 5 h. The solvent is removed under reduced pressure. The residue is dissolved in EE and is washed with sat. aq. NaHCO$_3$ solution and brine. Organic layers are separated, dried over MgSO$_4$, filtered and the solvent is removed under reduced pressure to afford 0.76 g of crude 2-[(1-methanesulfonyl-piperidin-4-yl)-methyl-amino]-2-methyl-propionic acid ethyl ester, which is used without further purification. ESI-MS: 307 [M+H]$^+$; HPLC (Rt): 1.09 min (method E)

Step 5: 2-[(1-Methanesulfonyl-piperidin-4-yl)-methyl-amino]-2-methyl-propionic acid 0.76 g (2.48 mmol) of 2-[(1-methanesulfonyl-piperidin-4-yl)-methyl-amino]-2-methyl-propionic acid ethyl ester are dissolved in EtOH (14.3 mL) and 3.72 mL (14.9 mmol) 4 N NaOH are added at RT. The reaction is refluxed for 16 h. The solvent is removed under reduced pressure, the residue is diluted with water and neutralized to pH 7 and lyophilized. The product is dissolved in acetone and filtered. The solvent is removed under reduced pressure to afford 0.26 g of 2-[(1-methanesulfonyl-piperidin-4-yl)-methyl-amino]-2-methyl-propionic acid. Yield: 37%; ESI-MS: 279 [M+H]$^+$; HPLC (Rt): 0.23 min (method D)

Intermediate 5: 2-Methyl-2-(4,4,4-trifluoro-butane-1-sulfonyl)-propionic acid For additional analytical data: see WO2010036630

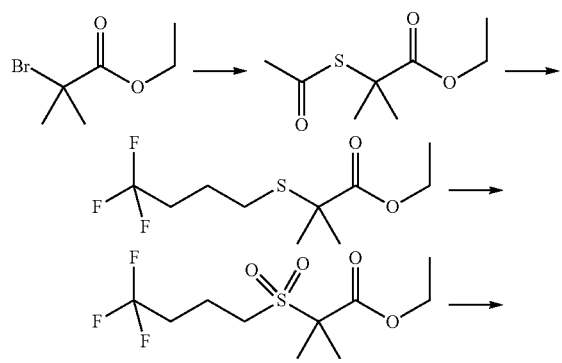

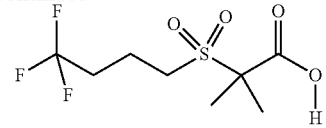

Step 1: 2-Acetylsulfanyl-2-methyl-propionic acid ethyl ester

To a solution of ethyl α-bromoisobutyrate (62 g, 0.32 mol) in DMF (500 mL) at room temperature is added potassium thioacetate (72 g, 0.63 mol). The reaction is stirred for 16 h and then concentrated under reduced pressure. The residue is diluted with a 2 M aq. HCl solution (500 mL) and extracted with EE (3×500 mL). The organic fractions are combined, washed with brine (300 mL), dried over MgSO$_4$, filtered and concentrated under reduced pressure. Purification by chromatography on silica eluting with heptanes/DCM provides 44 g of 2-acetylsulfanyl-2-methyl-propionic acid ethyl ester. Yield: 73%; ESI-MS: 191 [M+H]$^+$

Step 2: 2-Methyl-2-(4,4,4-trifluoro-butylsulfanyl)-propionic acid ethyl ester To a solution of 149 g (0.785 mol) of 2-acetylsulfanyl-2-methyl-propionic acid ethyl ester in EtOH (1.2 L, degassed under nitrogen for 1 h) are added 169.7 g (0.105 mol) of sodium methoxide, followed by a solution of 150 g (0.785 mol) of 4-bromo-1,1,1-trifluoro-butane. The reaction is heated to 85° C. for 3 d. The solvent is removed under reduced pressure. The residue is dissolved in DCM (1 L) and washed with saturated aq. NaHCO$_3$ solution (2×1 L). The organic layer is dried over Na$_2$SO$_4$, filtered and the filtrate is concentrated under reduced pressure to afford 171 g of 2-methyl-2-(4,4,4-trifluoro-butylsulfanyl)-propionic acid ethyl ester. Yield: 84%; ESI-MS: 259 [M+H]$^+$

Step 3: 2-Methyl-2-(4,4,4-trifluoro-butane-1-sulfonyl)-propionic acid ethyl ester To a solution of 220 g (0.852 mol) of 2-methyl-2-(4,4,4-trifluoro-butylsulfanyl)-propionic acid ethyl ester in dioxane/water (1/1, 4 L) are added 1047 g (1.703 mol) of OXONE® in portions over 0.5 h at RT. The reaction mixture is stirred at RT for 18 h. The solid is removed by filtration and rinsed with dioxane (0.5 L). The filtrate is concentrated under reduced pressure to remove the organic solvent. The aq. residue is extracted with DCM (2×1 L). The combined organic extracts are washed with saturated aq. NaHCO$_3$ solution (2 L), dried over Na$_2$SO$_4$ and filtered. The filtrate is concentrated under reduced pressure to afford 226 g of 2-methyl-2-(4,4,4-trifluoro-butane-1-sulfonyl)-propionic acid ethyl ester. Yield: 92%; ESI-MS: 291 [M+H]$^+$

Step 4: 2-Methyl-2-(3-methyl-butane-1-sulfonyl)-propionic acid

To a solution of 170 g (0.59 mol) of 2-methyl-2-(4,4,4-trifluoro-butane-1-sulfonyl)-propionic acid ethyl ester in THF (3.4 L) are added 225.4 g (1.76 mol) of potassium trimethylsilanolate in portions over 0.5 h. The reaction is stirred at room temperature for 18 h. The reaction mixture is acidified with 2 M aq. HCl solution (2 L) to pH 2 and extracted with DCM (2×2 L). The combined organic extracts are dried (Na$_2$SO$_4$) and filtered. The filtrate is concentrated under reduced pressure to afford 143 g of 2-methyl-2-(3-methyl-butane-1-sulfonyl)-propionic acid. Yield: 93%; ESI-MS: 261 [M–H]$^-$

Intermediate 6: 2-(5-Amino[1,3,4]thiadiazol-2-yl)-2-methyl-propionitrile

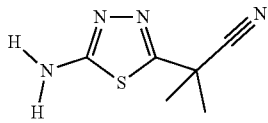

300 mg (3.29 mmol) of thiosemicarbazide and 370 mg (3.27 mmol) of 2-Cyano-2-methylpropanoic acid are dissolved in dioxane (10.0 mL) and heated to 90° C. 300 μL (3.29 mmol) of POCl₃ are added dropwise. The reaction is stirred at 90° C. for 1 h, cooled to RT and diluted with 1 N aq. HCl and DCM. The aq. layer is separated, 4 N aq. NaOH is added to reach pH 8 and then extracted with DCM. Then combined organic layer is washed with brine and dried. The solvent is removed under reduced pressure to afford 180 mg of 2-(5-amino[1,3,4]thiadiazol-2-yl)-2-methyl-propionitrile. Yield: 32%; ESI-MS: 169 [M+H]$^+$; HPLC (Rt): 0.24 min (method B)

Intermediate 7: 2-(5-Amino-isoxazol-3-yl)-2-methyl-propionitrile

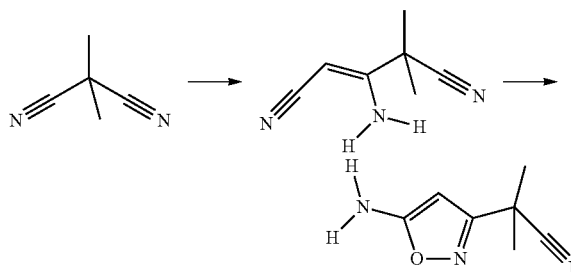

Step 1: 3-Amino-4,4-dimethyl-pent-2-endinitrile

A solution of potassium tert amylate in toluene (25%, 11.8 mL, 23 mmol) is added slowly to a solution of 2,2-Dimethyl-malononitrile (2.0 g, 21 mmol) and acetonitrile (1.2 mL, 23 mmol) in toluene (20 mL) at 40° C. under argon. The reaction mixture is stirred at 40° C. for 2 h and then cooled to 12° C. Water (5 mL) is added and the mixture is stirred at 20° C. for 15 min and at 2° C. for 30 min. Filtration, washing with cold water (10 mL) and drying under vacuum provides 2.30 g 3-Amino-4,4-dimethyl-pent-2-endinitrile. Yield: 80%: ESI-MS: 136 [M+H]$^+$; ¹H-NMR (DMSO-d6): 1.5, 4.1, 6.8 ppm.

Step 2: 2-(5-Amino-isoxazol-3-yl)-2-methyl-propionitrile

To 3-Amino-4,4-dimethyl-pent-2-endinitrile (10.0 g, 74 mmol) in MeOH (150 mL) is added NH₂OH·HCl (10.0 g, 144 mmol). The mixture is stirred at 40° C. for 7 h, concentrated, suspended in isopropyl acetate (100 mL) and washed with 4 N aq. NaOH (2×100 mL) and brine (50 mL). The extracted org. layer is concentrated to provide 7.40 g of 2-(5-Amino-isoxazol-3-yl)-2-methyl-propionitrile. Yield: 66%; ESI-MS: 152 [M+H]$^+$; ¹H-NMR (DMSO-d6): 1.6, 5.1, 6.8 ppm.

Preparation of Compounds of the Present Invention

Example 7: N-[5-(Cyano-dimethyl-methyl)-[1,3,4]thiadiazol-2-yl]-2-methyl-2-[methyl-(tetrahydro-pyran-4-ylmethyl)-amino]-propionamide

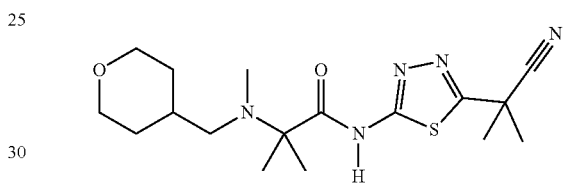

To 270 mg (1.25 mmol) of 2-methyl-2-[methyl-(tetrahydro-pyran-4-ylmethyl)-amino]-propionic acid (intermediate 3) in DMF (3 mL) are added 450 μL (2.58 mmol) DIPEA and 480 mg (1.26 mmol) HATU. In a second flask 110 mg sodium hydride (60% dispersion in oil; 2.75 mmol) are added to 215 mg (1.27 mmol) 2-(5-amino[1,3,4]thiadiazol-2-yl)-2-methyl-propionitrile (intermediate 6) in DMF (3 mL). After 10 min this mixture is added to the activated acid. The reaction mixture is stirred for additional 30 min, then filtered and purified by HPLC-MS to afford 50 mg of N-[5-(cyano-dimethyl-methyl)-[1,3,4]thiadiazol-2-yl]-2-methyl-2-[methyl-(tetrahydro-pyran-4-ylmethyl)-amino]-propionamide.

Yield: 11%; ESI-MS: 366 [M+H]$^+$; HPLC (Rt): 0.84 min (method A); ¹H-NMR (400 MHz, DMSO-d6): 0.92-1.04 (m, 2H), 1.25 (s, 6H), 1.68-1.76 (m, 3H), 1.83 (s, 6H), 2.09 (d, J=6.53 Hz, 2H), 2.20 (s, 3H), 3.23-3.33 (m, 4H), 3.79 (dd, J=11.6, 3.5 Hz, 2H), 11.55 (s, 1H) ppm.

The following examples are prepared in analogy to the above described procedure.

| Example | Structure | Yield (%) | ESI-MS [M + H]$^+$ | HPLC (Rt) | ¹H-NMR (400 MHz, DMSO-d6): |
|---|---|---|---|---|---|
| 8 | 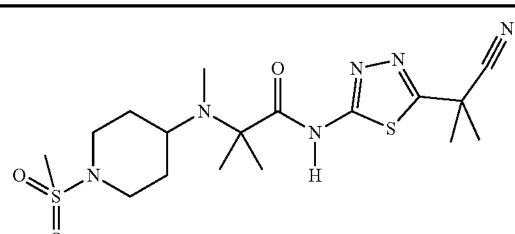 | 6 | 429 | 0.32 min (method B) | 1.30 (s, 6H), 1.60-1.79 (m, 4H), 1.83 (s, 6H), 2.19 (s, 3H), 2.50-2.63 (m, 1H) 2.65-2.74 (m, 2H), 2.81 (s, 3H), 3.51-3.58 (m, 2H), 11.80 (s, 1H) ppm. |

| Example | Structure | Yield (%) | ESI-MS [M + H]+ | HPLC (Rt) | 1H-NMR (400 MHz, DMSO-d6): |
|---|---|---|---|---|---|
| 4 | 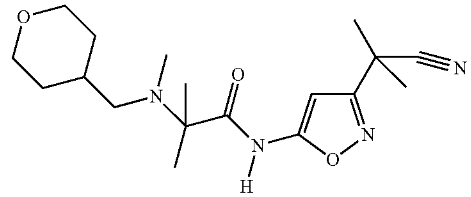 [SMILES: CN(CC1CCOCC1)C(C)(C)C(=O)Nc1cc(C(C)(C)C#N)no1] | 16 | 349 | 0.74 min (method H) | 0.91-1.04 (m, 2H), 1.19 (s, 6H), 1.68-1.75 (m, 3H), 1.69 (s, 6H), 2.05 (d, J = 6.38 Hz, 2H), 2.16 (s, 3H), 3.24-3.30 (m, 2H), 3.81 (dd, J = 11.4, 3.6 Hz, 2H), 6.44 (s, 1H), 10.9 (s, 1H) ppm. |
| 5 | 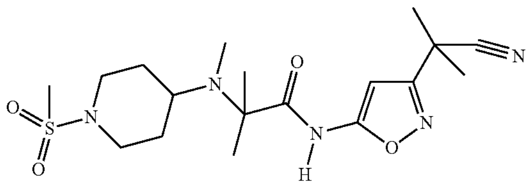 [SMILES: CN(C1CCN(S(C)(=O)=O)CC1)C(C)(C)C(=O)Nc1cc(C(C)(C)C#N)no1] | 30 | 412 | 0.66 min (method H) | 1.25 (s, 6H), 1.62-1.78 (m, 4H), 1.69 (s, 6H), 2.17 (s, 3H), 2.50-2.55 (m, 1H), 2.65-2.74 (m, 2H), 2.81 (s, 3H), 3.51-3.58 (m, 2H), 6.44 (s, 1H), 11.15 (s, 1H) ppm. |

Example 1: N-[3-(Cyano-dimethyl-methyl)-isoxazol-5-yl]-2-methyl-2-(4,4,4-trifluoro-butane-1-sulfonyl)-propionamide

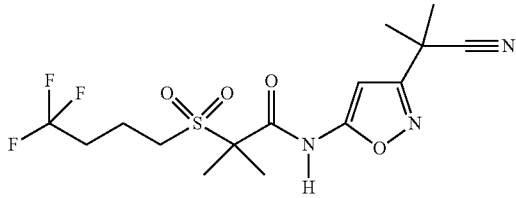 [SMILES: CC(C)(C#N)c1cc(NC(=O)C(C)(C)S(=O)(=O)CCCC(F)(F)F)on1]

To 100 mg (0.38 mmol) of 2-methyl-2-(4,4,4-trifluoro-butane-1-sulfonyl)-propionic acid (intermediate 5) in toluene (4.07 mL) are added 55.3 µL (0.76 mmol) thionyl chloride and 3.10 µL (0.04 mmol) DMF. The solution is stirred at reflux for 1 h. In a second flask 78.7 µL (0.46 mmol) DIPEA are added to 63.4 mg (0.42 mmol) of 2-(5-amino-isoxazol-3-yl)-2-methyl-propionitrile (intermediate 7) in toluene (2.03 mL). The mixture is stirred at RT for 5 min, then added to the acid chloride and stirring is continued at RT for 16 h. The reaction mixture is purified by HPLC-MS to afford 78.7 mg of N-[3-(cyano-dimethyl-methyl)-isoxazol-5-yl]-2-methyl-2-(4,4,4-trifluoro-butane-1-sulfonyl)-propionamide. Yield: 52%; ESI-MS: 396 [M+H]+; HPLC (Rt): 1.14 min (method G); 1H-NMR (400 MHz, DMSO-d6): 1.68 (s, 6H), 1.70 (s, 6H), 1.86-1.91 (m, 2H), 2.47-2.52 (m, 2H), 3.34-3.40 (m, 2H), 6.57 (s, 1H), 11.64 (s, 1H) ppm.

Example 2: N-[3-(Cyano-dimethyl-methyl)-isoxazol-5-yl]-2-methyl-2-(tetrahydro-pyran-4-ylmethanesulfonyl)-propionamide

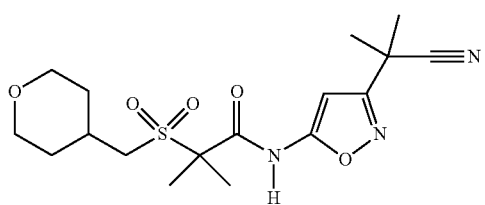 [SMILES: CC(C)(C#N)c1cc(NC(=O)C(C)(C)S(=O)(=O)CC2CCOCC2)on1]

Prepared according to procedure of example 1 starting from 100 mg (0.40 mmol) of 2-methyl-2-(tetrahydro-pyran-4-ylmethanesulfonyl)-propionic acid (intermediate 2) and 66.4 mg (0.44 mmol) 2-(5-amino-isoxazol-3-yl)-2-methyl-propionitrile (intermediate 7).

Yield: 48%; ESI-MS: 384 [M+H]+; HPLC (Rt): 0.96 min (method G); 1H-NMR (400 MHz, DMSO-d6): 1.32-1.42 (m, 2H), 1.67 (s, 6H), 1.70-1.76 (m, 2H), 1.70 (s, 6H), 2.12-2.24 (m, 1H), 2.48-2.51 (m, 2H), 3.19 (d, J=6.81 Hz, 2H), 3.26-3.34 (m, 2H), 6.59 (s, 1H), 11.57 (s, 1H) ppm.

Example 6: (S)-1-(Tetrahydro-pyran-4-yl)-pyrrolidine-2-carboxylic acid[3-(cyano-dimethyl-methyl)-isoxazol-5-yl]-amide

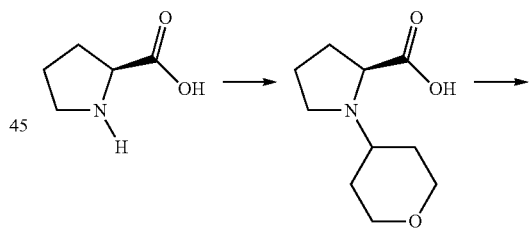

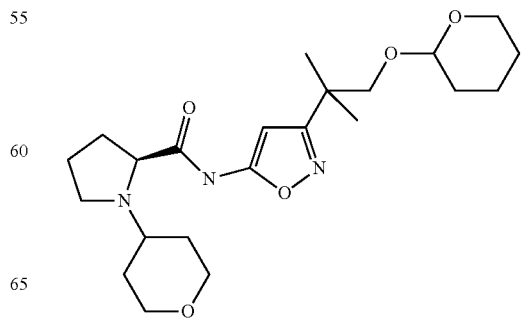

-continued

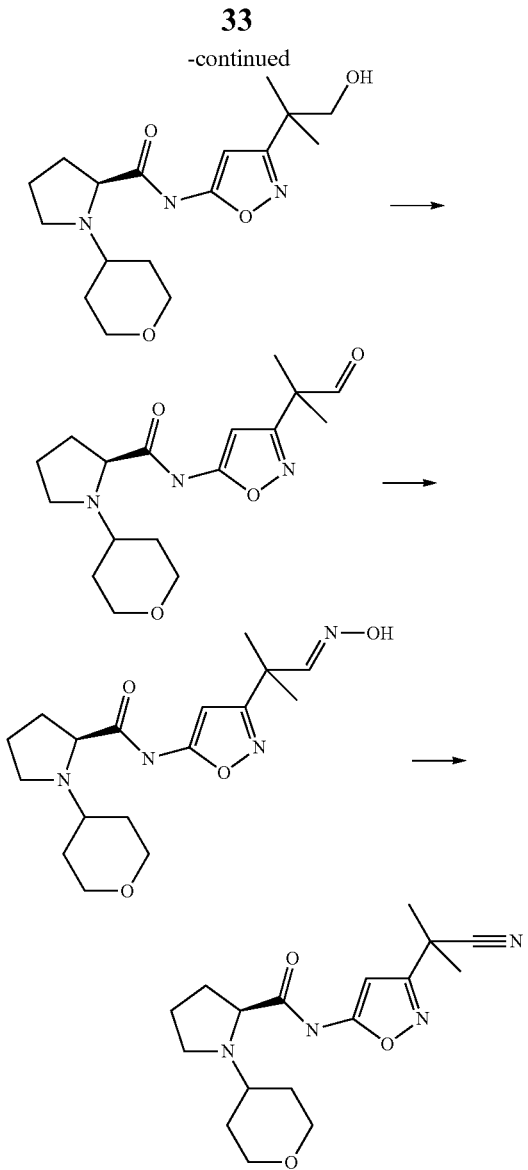

Step 1: (S)-1-(Tetrahydro-pyran-4-yl)-pyrrolidine-2-carboxylic acid

To L-proline (1.00 g; 8.69 mmol) in 1,2-dichloroethane (10 mL) acetic acid (1.98 mL; 33.0 mmol)) is added tetrahydro-pyran-4-one (0.87 g; 8.69 mmol) and $Na_2SO_4$ (~10 equivalents). After 45 minutes of agitation on an orbital shaker, Mp-triacetoxyborohydride resin (4.27 g; 10.42 mmol) is added. The mixture is agitated at RT overnight and filtered and the resin washed with DCM. The combined filtrate is washed with aq. sat. $NaHCO_3$ solution and brine, dried ($Na_2SO_4$), filtered and concentrated in vacuo. Excess acetic acid is removed by successive azeotropic distillation with toluene on the rotary evaporator to afford (S)-1-(tetrahydro-pyran-4-yl)-pyrrolidine-2-carboxylic acid. ESI-MS: 200 $[M+H]^+$

Step 2: (S)-1-(Tetrahydro-pyran-4-yl)-pyrrolidine-2-carboxylic acid (3-[1,1-dimethyl-2-(tetrahydro-pyran-2-yloxy)-ethyl]-isoxazol-5-yl)-amide To 1.20 g (6.02 mmol) of (S)-1-(tetrahydro-pyran-4-yl)-pyrrolidine-2-carboxylic acid in DMF (50 mL) are added 3.67 mL (21.1 mmol) diisopropyl-ethyl-amine and 3.44 g (9.03 mmol) of HATU. The solution is stirred at RT for 1 h. In a second flask to 1.45 g (6.02 mmol) of 3-[1,1-dimethyl-2-(tetrahydro-pyran-2-yloxy)-ethyl]-isoxazol-5-ylamine (intermediate 7a) in DMF (25 mL) are added 602 mg sodium hydride (60% dispersion in oil; 15.1 mmol) under cooling by an ice bath. Then this solution is added to the activated acid and stirring is continued for 48 h. The reaction mixture is purified by HPLC-MS to afford 0.51 g of (S)-1-(tetrahydro-pyran-4-yl)-pyrrolidine-2-carboxylic acid (3-[1,1-dimethyl-2-(tetrahydro-pyran-2-yloxy)-ethyl]-isoxazol-5-yl)-amide. Yield: 20%; ESI-MS: 422 $[M+H]^+$; HPLC (Rt): 1.55 min (method C)

Step 3: (S)-1-(Tetrahydro-pyran-4-yl)-pyrrolidine-2-carboxylic acid [3-(2-hydroxy-1,1-dimethyl-ethyl)-isoxazol-5-yl]-amide To 400 mg (0.95 mmol) of (S)-1-(tetrahydro-pyran-4-yl)-pyrrolidine-2-carboxylic acid (3-[1,1-dimethyl-2-(tetrahydro-pyran-2-yloxy)-ethyl]-isoxazol-5-yl)-amide in EtOH (6.00 mL) are added 119 mg (0.47 mmol) pyridinium-p-toluenesulfonate. The reaction is stirred at 75° C. for 28 h. The reaction mixture is purified by HPLC-MS to afford 240 mg of (S)-1-(tetrahydro-pyran-4-yl)-pyrrolidine-2-carboxylic acid [3-(2-hydroxy-1,1-dimethyl-ethyl)-isoxazol-5-yl]-amide. Yield: 75%; ESI-MS: 338 $[M+H]^+$; HPLC (Rt): 0.82 min (method D)

Step 4: (S)-1-(Tetrahydro-pyran-4-yl)-pyrrolidine-2-carboxylic acid [3-(1,1-dimethyl-2-oxo-ethyl)-isoxazol-5-yl]-amide To 180 mg (0.53 mmol) of (S)-1-(tetrahydro-pyran-4-yl)-pyrrolidine-2-carboxylic acid [3-(2-hydroxy-1,1-dimethyl-ethyl)-isoxazol-5-yl]-amide in DCM (1.74 mL) are added 317 mg (0.75 mmol) of (1,1,1-triacetoxy-1,1-dihydro-1,2-benziodoxol-3(1H)-one (Dess-Martin-periodinane). The reaction mixture is stirred at RT for 1 h, diluted with sat. aq. $NaHCO_3$ solution and stirred for additional 30 min. The layers are separated; the organic layer is washed with brine and dried over $Na_2SO_4$. The solvent is removed under reduced pressure, the residue is purified by silica gel chromatographie (eluent: EE) to afford 93.0 mg of (S)-1-(tetrahydro-pyran-4-yl)-pyrrolidine-2-carboxylic acid [3-(1,1-dimethyl-2-oxo-ethyl)-isoxazol-5-yl]-amide. Yield: 52%; ESI-MS: 336 $[M+H]^+$; HPLC (Rt): 1.12 min (method E)

Step 5: (S)-1-(Tetrahydro-pyran-4-yl)-pyrrolidine-2-carboxylic acid [3-(2-hydroxyimino-1,1-dimethyl-ethyl)-isoxazol-5-yl]-amide To 90.0 mg (0.27 mmol) of (S)-1-(tetrahydro-pyran-4-yl)-pyrrolidine-2-carboxylic acid [3-(1,1-dimethyl-2-oxo-ethyl)-isoxazol-5-yl]-amide in MeOH (3.00 mL) are added 22.4 mg (0.32 mmol) hydroxylamine hydrochloride and 58.5 µL (0.72 mmol) pyridine. The reaction is stirred at 60° C. for 3 h. The solvent is removed under reduced pressure and the residue is purified by HPLC-MS to afford 79.0 mg of (S)-1-(tetrahydro-pyran-4-yl)-pyrrolidine-2-carboxylic acid [3-(2-hydroxyimino-1,1-dimethyl-ethyl)-isoxazol-5-yl]-amide. Yield: 84%; ESI-MS: 351 $[M+H]^+$; HPLC (Rt): 1.04 min (method E)

Step 6: (S)-1-(Tetrahydro-pyran-4-yl)-pyrrolidine-2-carboxylic acid[3-(cyano-dimethyl-methyl)-isoxazol-5-yl]-amide 79.0 mg (0.23 mmol) of (S)-1-(tetrahydro-pyran-4-yl)-pyrrolidine-2-carboxylic acid [3-(2-hydroxyimino-1,1-dimethyl-ethyl)-isoxazol-5-yl]-amide are added to 1.00 mL trifluoroacetic anhydride and stirred at 100° C. for 3 h. The solvent is removed under reduced pressure. The residue is purified by HPLC-MS to afford 32.6 mg of (S)-1-(tetrahydro-pyran-4-yl)-pyrrolidine-2-carboxylic acid[3-(cyano-dimethyl-methyl)-isoxazol-5-yl]-amide. Yield: 44%; ESI-MS: 333 [M+H]⁺; HPLC (Rt): 0.66 min (method F); ¹H-NMR (400 MHz, DMSO-d6): 1.31-1.53 (m, 2H), 1.57-1.65 (m, 1H), 1.69 (s, 6H), 1.69-1.81 (m, 4H), 2.01-2.14 (m, 1H), 2.50-2.66 (m, 2H), 3.08-3.14 (m, 1H), 3.20-3.32 (m, 2H), 3.47-3.52 (m, 1H), 3.77-3.88 (m, 2H), 6.46 (s, 1H), 9.70 (s, 1H) ppm.

Example 3: N-[3-(Cyano-dimethyl-methyl)-isoxazol-5-yl]-2-(tetrahydro-pyran-4-sulfonyl)-propionamide

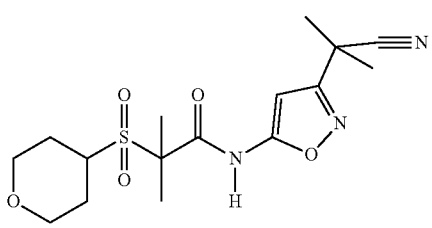 [SMILES: CC(C)(C#N)c1cc(NC(=O)C(C)(C)S(=O)(=O)C2CCOCC2)on1]

To 3.43 g (14.6 mmol) 2-Methyl-2-(tetrahydro-pyran-4-sulfonyl)-propionic acid (intermediate 1) in 38 mL toluene and 17 μL pyridine at 90° C. is added 2.60 g (21.8 mmol) SOCl₂ dropwise within 20 min and stirring is continued for 2 h at 90° C. The solvent is evaporated under reduced pressure and the residue is coevaporated twice with toluene (16 mL each) to afford the crude acid chloride. To 2.00 g 2-(5-Amino-isoxazol-3-yl)-2-methyl-propionitrile (13.2 mmol, intermediate 7) in 14 mL toluene is added 3.80 mL (21.8 mmol) DIPEA. To this mixture at 60° C. is added dropwise a mixture of the acid chloride in 16 mL toluene within 10 min and stirring is continued overnight at 50° C. After addition of water (24 mL) the mixture is heated to 70° C. for 2 h and then allowed to cool to RT. The precipitate is filtered, washed with water (2×8 mL) and dried at 50° C. to afford 3.43 g of N-[3-(Cyano-dimethyl-methyl)-isoxazol-5-yl]-2-(tetrahydro-pyran-4-sulfonyl)-propionamide.

Yield: 70%; ESI-MS: 370 [M+H]⁺; HPLC (Rt): 0.89 min (method F); ¹H-NMR (400 MHz, DMSO-d6): 1.62-1.72 (m, 2H), 1.69 (s, 6H), 1.70 (s, 6H), 1.80-1.87 (m, 2H), 3.30-3.42 (m, 3H), 3.86-3.93 (m, 2H), 6.57 (s, 1H), 11.57 (s, 1H) ppm.

The invention claimed is:

1. A method of treating pain selected from the group consisting of acute pain, visceral pain, and neuropathic pain, comprising administering to a human being an effective amount of a pharmaceutical composition comprising a compound selected from the group consisting of

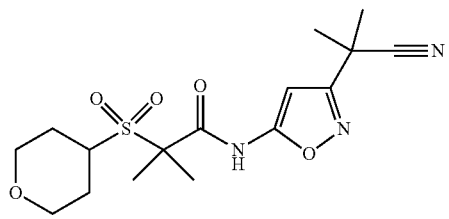 [SMILES: CC(C)(C#N)c1cc(NC(=O)C(C)(C)S(=O)(=O)C2CCOCC2)on1]

and a pharmaceutically acceptable salt thereof in admixture with a pharmaceutically acceptable adjuvant, diluent and/or carrier, to treat the pain.

2. The method of claim 1, wherein the compound is

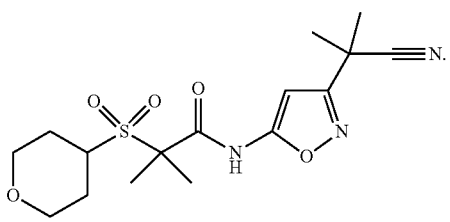 [SMILES: CC(C)(C#N)c1cc(NC(=O)C(C)(C)S(=O)(=O)C2CCOCC2)on1]

3. The method of claim 1, wherein the pain is acute pain.
4. The method of claim 2, wherein the pain is acute pain.
5. The method of claim 3, wherein the acute pain is trigeminal neuralgia.
6. The method of claim 4, wherein the acute pain is trigeminal neuralgia.
7. The method of claim 1, wherein the pain is visceral pain.
8. The method of claim 2, wherein the pain is visceral pain.
9. The method of claim 1, wherein the pain is neuropathic pain.
10. The method of claim 2, wherein the pain is neuropathic pain.
11. The method of claim 9, wherein the neuropathic pain is post-herpetic neuralgia.
12. The method of claim 10, wherein the neuropathic pain is post-herpetic neuralgia.
13. The method of claim 9, wherein the neuropathic pain is due to chemotherapy caused nerve injury.
14. The method of claim 10, wherein the neuropathic pain is due to chemotherapy caused nerve injury.
15. The method of claim 9, wherein the neuropathic pain is due to central nervous system injury.
16. The method of claim 10, wherein the neuropathic pain is due to central nervous system injury.
17. The method of claim 9, wherein the neuropathic pain is due to diabetic neuropathy.
18. The method of claim 10, wherein the neuropathic pain is due to diabetic neuropathy.
19. The method of claim 9, wherein the neuropathic pain is due to diabetic peripheral neuropathy.
20. The method of claim 10, wherein the neuropathic pain is due to diabetic peripheral neuropathy.

* * * * *